US010149644B2

(12) United States Patent
Ran et al.

(10) Patent No.: US 10,149,644 B2
(45) Date of Patent: Dec. 11, 2018

(54) CURCUMIN DERIVATIVES FOR AMYLOID-β PLAQUE IMAGING

(71) Applicant: The General Hospital Corporation, Boston, MA (US)

(72) Inventors: Chongzhao Ran, Winchester, MA (US); Anna Moore, Stoneham, MA (US)

(73) Assignee: The General Hospital Corporation, Boston, MA (US)

( * ) Notice: Subject to any disclaimer, the term of this patent is extended or adjusted under 35 U.S.C. 154(b) by 80 days.

(21) Appl. No.: 14/515,665

(22) Filed: Oct. 16, 2014

(65) Prior Publication Data

US 2015/0087937 A1 Mar. 26, 2015

Related U.S. Application Data

(62) Division of application No. 13/056,228, filed as application No. PCT/US2009/052335 on Jul. 31, 2009, now abandoned.

(60) Provisional application No. 61/085,076, filed on Jul. 31, 2008.

(51) Int. Cl.

| | |
|---|---|
| ***A61K 51/00*** | (2006.01) |
| ***A61M 36/14*** | (2006.01) |
| ***A61B 5/00*** | (2006.01) |
| ***A61K 49/00*** | (2006.01) |
| ***A61K 51/04*** | (2006.01) |
| ***G01N 33/68*** | (2006.01) |
| ***A61B 5/145*** | (2006.01) |
| ***A61B 5/1455*** | (2006.01) |
| ***A61B 6/03*** | (2006.01) |
| ***A61M 5/00*** | (2006.01) |
| ***G01R 33/56*** | (2006.01) |

(52) U.S. Cl.

CPC .......... *A61B 5/4088* (2013.01); *A61B 5/1455* (2013.01); *A61B 5/14546* (2013.01); *A61B 6/037* (2013.01); *A61K 49/0002* (2013.01); *A61K 49/0021* (2013.01); *A61K 51/0455* (2013.01); *A61M 5/007* (2013.01); *G01N 33/6896* (2013.01); *G01R 33/5601* (2013.01); *G01N 2333/4709* (2013.01); *G01N 2800/28* (2013.01); *G01N 2800/2821* (2013.01)

(58) Field of Classification Search

CPC .............. A61B 5/4088; A61K 49/0021; G01N 2800/2821

USPC ........................................................ 424/1.89

See application file for complete search history.

(56) References Cited

U.S. PATENT DOCUMENTS

| | | | | |
|---|---|---|---|---|
| 4,522,811 | A | 6/1985 | Eppstein et al. | |
| 6,468,798 | B1 | 10/2002 | Debs et al. | |
| 6,471,996 | B1 | 10/2002 | Sokoll et al. | |
| 6,472,375 | B1 | 10/2002 | Hoon et al. | |
| 6,503,713 | B1 | 1/2003 | Rana | |
| 6,881,584 | B1 | 4/2005 | Lenhard et al. | |
| 6,983,753 | B1 | 1/2006 | Lenhard et al. | |
| 7,277,744 | B2 | 10/2007 | Schaefer et al. | |
| 2007/0060644 | A1* | 3/2007 | Vander Jagt et al. | ........ 514/475 |
| 2008/0033055 | A1 | 2/2008 | Miller et al. | |
| 2008/0146660 | A1 | 6/2008 | Lee et al. | |
| 2008/0161391 | A1 | 7/2008 | Lee et al. | |
| 2010/0216859 | A1 | 8/2010 | Chen | |
| 2011/0208064 | A1 | 8/2011 | Ran et al. | |
| 2014/0275969 | A1 | 9/2014 | Lau | |
| 2015/0158841 | A1 | 6/2015 | Ran et al. | |

FOREIGN PATENT DOCUMENTS

| | | |
|---|---|---|
| CN | 102603782 | 7/2012 |
| WO | WO 2010/074971 | 1/2010 |
| WO | WO2010/017094 | 2/2010 |
| WO | WO 2010/068935 | 6/2010 |
| WO | WO 2010/132815 | 11/2010 |
| WO | WO 2011014648 | 2/2011 |

OTHER PUBLICATIONS

Garcia-Alloza et al. J. Neurochem. 2007, 102, 1095-1104.*
Yang et al. J. Biol. Chem. 2005, 280, 5892-5901.*
Ryu et al. J. Med. Chem. 2006, 49, 6111-6119.*
Ulrich et al. Angew. Chem. Int. Ed. 2008, 47, 1184-1201.*
Massoud et al. Genes and Develop. 2003, 17, 545-580.*
Zhang et al. J. Am. Chem. Soc. 2007, 129, 8942-8943.*
Harmon and Abumrad, "Binding of sulfosuccinimidyl fatty acids to adipocyte membrane proteins: Isolation and ammo-terminal sequence of an 88-kD protein implicated in transport of long-chain fatty acids," J Membr Biol., Apr. 1993, 133(1):43-9.
Haucke et al., "The effect of internal rotation on absorption and fluorescence of dye molecules," Journal of Molecular Structure, Mar. 1990, 219: 411-416.
Herrero et al "Inflammation and adipose tissue macrophages in lipodystrophic mice," PNAS, Jan. 2010, 107: 240-245.
Himms-Hagen et al., "Multilocular fat cells in WAT of CL-316243-treated rats derive directly from white adipocytes," American Journal of Physiology Cell Physiology, 2000, 279: C670-681.
Hu et al., "Identification of brown adipose tissue in mice with fat-water IDEAL-MRI," Journal of Magnetic Resonance Imaging, 2010, 31: 1195-1202.
International Preliminary Report on Patentability in International Application No. PCT/US2013/053833, dated Feb. 10, 2015, 7 pages.

(Continued)

*Primary Examiner* — Michael G Hartley
*Assistant Examiner* — Sean R Donohue
(74) *Attorney, Agent, or Firm* — Fish & Richardson P.C.

(57) ABSTRACT

The present invention provides curcumin-derived near infrared (NIR) imaging probes. Upon interacting with amyloid β aggregates, these probes undergo a range of changes, qualifying them as "smart" probes. The inventors have demonstrated that probes of the invention have the capacity to monitor the progression of Alzheimer's disease in an in vivo animal model. In addition, the present invention encompasses probes useful as PET imaging agents, MRI imaging agents and multimodal imaging agents, as well as related methods of detecting and imaging amyloid β aggregates and plaques.

12 Claims, 13 Drawing Sheets

(56) References Cited

OTHER PUBLICATIONS

International Preliminary Report on Patentability in International Application No. PCT/US2014/054012, dated Mar. 8, 2016, 9 pages.
International Search Report and Written Opinion in International Application No. PCT/US2014/054012, dated Nov. 25, 2014, 15 pages.
International Search Report and Written Opinion dated Dec. 5, 2013 in international application No. PCT?US2013/053833, 10 pages.
Jamal and Saggerson, "Changes in brown-adipose-tissue mitochondrial processes in streptozotocin-diabetes," The Biochemical Journal, 1988, 252: 293-296.
Kajimura et al., "Regulation of the brown and white fat gene programs through a PRDM16/CtBP transcriptional complex," Genes & Development, 2008, 22: 1397-1409.
Kaplan et al., "Membrane proteins and urea and acetamide transport in the human erythrocyte," J. Membr Biol., Dec. 1975, 20:181-190.
Khanna and Branca, "Detecting brown adipose tissue activity with BOLD MRI in mice," Magnetic Resonance in Medicine, Oct. 2012, 68: 1285-1290.
Kim et al, "Effect of adipocyte beta3-adrenergic receptor activation on the type 2 diabetic MKR mice," American Journal of Physiology Endocrinology and Metabolism, Jun. 2006, 290: E1227-1236.
Madar et al., "18F-fluorobenzyl triphenyl phosphonium: a noninvasive sensor of brown adipose tissue thermogenesis," Journal of Nuclear Medicine, May 2011, 52(5): 808-814.
Mattson, "Does brown fat protect against diseases of aging?," Ageing Research Reviews, Jan. 2010, 9: 69-76.
Nagajyothi et al., "Response of adipose tissue to early infection with Trypanosoma cruzi (Brazil strain)," The Journal of Infectious Diseases, 2012, 205: 830-840.
Nedergaard et al, "Unexpected evidence for active brown adipose tissue in adult humans," American Journal of Physiology Endocrinology and Metabolism, 2007, 293: E444-452.
Ocloo et al, "Cold-induced alterations of phospholipid fatty acyl composition in brown adipose tissue mitochondria are independent of uncoupling protein-1," American Journal of Physiology Regulatory, Integrative and Comparative Physiology, Sep. 2007, 293(3): R1 086-1093.
Ouellet et al., "Brown adipose tissue oxidative metabolism contributes to energy expenditure during acute cold exposure in humans," The Journal of Clinical Investigation, 2012, 122: 545-552.
Pfannenberg et al., "Impact of age on the relationships of brown adipose tissue with sex and adiposity in humans," Diabetes, Jul. 2010, 59: 1789-1793.
Popic et al., "An Improved Synthesis of 2-diazo-1,3-diketones," Synthesis, 1991, 3:195-8.
Qiang et al., "Brown Remodeling of White Adipose Tissue by SirT1-Dependent Deacetylation of Ppary," Cell, Aug. 2012, 150: 620-632.
Ran and Moore, "Spectral Unmixing Imaging of Wavelength-Responsive Fluorescent Probes: An Application for the Real-Time Report of Amyloid Beta Species in Alzheimer's Disease," Mol. Imaging Biol., Jun. 2012, 14(3): 293-300.
Ran et al., "Design, synthesis, and testing of difluoroboron derivatized curcumins as near infrared probes for in vivo detection of amyloid-β deposits," Journal of the American Chemical Society, Oct. 2009, 131(42): 15257-15261.
Ran et al., "Non-conjugated small molecule FRET for differentiating monomers from higher molecular weight amyloid beta species," PLoS One. Apr. 29, 2011;6(4):e19362, 6 pages.
Ravin, "Preformulation," Remington's Pharmaceutical Sciences, 17th ed., Mack Publishing Company, Easton, Pa., 1985, pp. 1409-1418.
Richard and Picard, "Brown fat biology and thermogenesis," Frontiers in Bioscience, Jan. 2011, 16: 1233-1260.
Sandoval et al., "Fatty acid transport and activation and the expression patterns of genes involved in fatty acid trafficking," Arch. Biochem. Biophysics, Sep. 2008, 477:363-371.
Schulz et al., "Brown-fat paucity due to impaired BMP signalling induces compensatory browning of white fat," Nature, Mar. 2013, 495: 379-383.
Seydoux et al., "Brown adipose tissue metabolism in streptozotocin-diabetic rats," Endocrinology, 1983, 113: 604-610.
Shoup et al., "F-18 labeled bis-dialkylamino-curcuminoid as a potential amyloid-beta imaging agent," J Nucl Med, May 2011; 52:1538.
Tatsumi et al., "Intense (18)F-FDG uptake in brown fat can be reduced pharmacologically," Journal of Nuclear Medicine, Jul. 2004, 45(7): 1189-1193.
Tran and Kahn, "Transplantation of adipose tissue and stem cells: role in metabolism and disease," Nature Reviews Endocrinology, Apr. 2010, 6: 195-213.
Tseng et al., "New role of bone morphogenetic protein 7 in brown adipogenesis and energy expenditure," Nature, Aug. 2008, 454: 1000-1004.
van Marken Lichtenbelt et al., "Cold-activated brown adipose tissue in healthy men," The New England Journal of Medicine, Apr. 2009, 360: 1500-1508.
Weissleder, "A clearer vision for in vivo imaging," Nature Biotechnology, Apr. 2001, 19:316-317.
Williams and Fisher, "Globular warming: how fat gets to the furnace," Nat. Med., Feb. 2011, 17: 157-159.
Wilson-Fritch et al., "Mitochondrial remodeling in adipose tissue associated with obesity and treatment with rosiglitazone," The Journal of Clinical Investigation , Nov. 2004,114(9): 1281-1289.
Wu et al., "Brown adipose tissue can be activated or inhibited within an hour before 18F-FDG injection: a preliminary study with microPET," Journal of Biomedicine & Biotechnology, 2011, 2011: 159834.
Xu et al., "Exercise ameliorates high-fat diet-induced metabolic and vascular dysfunction, and increases adipocyte progenitor cell population in brown adipose tissue," American Journal of Physiology Regulatory, Integrative and Comparative Physiology, 2011, 300: R1115-1125.
Yoneshiro et al., "Age-related decrease in cold-activated brown adipose tissue and accumulation of body fat in healthy humans," Obesity, Sep. 2011, 19: 1755-1760.
Zhang et al, "Cross talk between insulin and bone morphogenetic protein signaling systems in brown adipogenesis," Molecular and Cellular Biology, Sep. 2010, 30: 4224-4233.
Zhang, "In Vivo Optical Imaging of Interscapular Brown Adipose Tissue with 18F-FDG via Cerenkov Luminescence Imaging," Plos One, Apr. 2013, 8(4): e62007.
Zhou et al., "CD36 level and trafficking are determinants of lipolysis in adipocytes," FASEB J., Nov. 2012, 26(11):4733-42.
FDA-approved radiopharmaceuticals, Cardinal Health, Jun. 2016, pp. 1-6.
Office Action in U.S. Appl. No. 14/419,985, dated Nov. 18, 2016, 9 pages.
Office Action in U.S. Appl. No. 14/916,779, dated Oct. 24, 2016, 18 pages.
Wang et al., "In Vivo Imaging of Histone Deacetylases (HDACs) in the Central Nervous System and Major Peripheral Organs," J Med Chem, 2014, 57: 7999-8009.
Aleo et al., "Mechanism and Implications of Brown Adipose Tissue Proliferation in Rats and Monkeys Treated with the Thiazolidinedione Darglitazone, a Potent Peroxisome Proliferator-Activated Receptor-γ Agonist," The Journal of Pharmacology and Experimental Therapeutics, 2003, 305:1173-1182.
Baranova et al., "CD36 Is a Novel Serum Amyloid A (SAA) Receptor Mediating SAA Binding and SAA-induced Signaling in Human and Rodent Cells," J Biol Chem, Mar. 2010, 285(11):8492-8506.
Bartelt et al., "Brown adipose tissue activity controls triglyceride clearance," Nature Medicine, Feb. 2011, 17(2): 200-205.
Basu, "Functional imaging of brown adipose tissue with PET: can this provide new insights into the pathophysiology of obesity and thereby direct antiobesity strategies?," Nuclear Medicine Communications, 2008, 29(11): 931-933.
Berge et al., "Pharmaceutical Salts," J Pharmaceutical Sci, 66(1):1-19 (1977).

(56) References Cited

OTHER PUBLICATIONS

Boss and Farmer, "Recruitment of brown adipose tissue as a therapy for obesity-associated diseases," Frontiers in Endocrinology, Feb. 2012, 3: 118-123.
Bostrom et al., "A PGC1α-dependent myokine that drives browning of white fat and thermogenesis," Nature, 481: 463-468.
Burcelin et al., "Changes in uncoupling protein and GLUT4 glucose transporter expressions in interscapular brown adipose tissue of diabetic rats: relative roles of hyperglycaemia and hypoinsulinaemia," The Biochemical Journal, 1993, 291: 109-113.
Cannon and Nedergaard, "Brown adipose tissue: function and physiological significance," Physiological Reviews, Jan. 2004, 84: 277-359.
Chen et al., "Anatomical and Functional Assessment of Brown Adipose Tissue by Magnetic Resonance Imaging. Obesity," Jul. 2012, 20(7): 1519-1526.
Coburn et al., "Role of CD36 in membrane transport and utilization of long-chain fatty acids by different tissues," J Mol Neurosci., 2001, 16(2-3):117-121.
Cypess et al., "Identification and importance of brown adipose tissue in adult humans," The New England Journal of Medicine, Apr. 2009,360: 1509-1517.
Czarnik, "Encoding methods for combinatorial chemistry," Curr. Opin. Chem. Bio., Jun. 1997, 1:60-6.
Demers et al., "Identification of the growth hormone-releasing peptide binding site in CD36: a photoaffinity cross-linking study," Biochem. J., 2004, 382:417-424.
Farmer, "Molecular determinants of brown adipocyte formation and Function," Genes & Development, 2008, 22: 1269-1275.
Greenwalt et al., "Heart CD36 Expression Is Increased in Murine Models of Diabetes and in Mice Fed a High Fat Diet," J Clin Invest., 1995, 96(3):1382-1388.
Gunawardana and Piston, "Reversal of type 1 diabetes in mice by brown adipose tissue transplant," Diabetes, Mar. 2012, 61: 674-682.
Hamajima et al., "Intranasal administration of HIV-DNA vaccine formulated with a polymer, carboxymethylcellulose, augments mucosal antibody production and cell-mediated immune response," Clin Immunol Immunopathol. Aug. 1998;88(2):205-10.

* cited by examiner

C

CURCUMIN DERIVATIVES FOR AMYLOID-β PLAQUE IMAGING

CROSS-REFERENCE TO RELATED APPLICATIONS

This application is a divisional application of U.S. application Ser. No. 13/056,228, filed Apr. 21, 2011, which represents the U.S. National Stage of PCT/US2009/052335, filed Jul. 31, 2009, which claims the benefit of U.S. Provisional Application 61/085,076, filed Jul. 31, 2008. All the above applications are incorporated by reference herein.

STATEMENT REGARDING FEDERALLY SPONSORED RESEARCH OR DEVELOPMENT

Not Applicable.

FIELD OF THE INVENTION

The invention relates generally to molecular probes for amyloid-β plaque imaging. In particular, the invention is related to various curcumin derivatives useful for imaging amyloid-β plaques in human subjects.

BACKGROUND OF THE INVENTION

Amyloid-β (Aβ) deposits are a well known pathological hallmark for Alzheimer's disease (AD). Their formations arise from aggregated peptides Aβ40 and Aβ42, which are generated from amyloid peptide precursor (APP) by cleaving with β- and γ-secretases {11; 15}. Normally, the concentrations of the generated Aβ40 and Aβ42 monomers are maintained at a reasonable level through the balance between generation and clearance. Upon the initiation of AD, however, the equilibrium moves towards accumulating of Aβ monomers. Consequently, the monomers begin to form fibrils upon stimulation with various factors such as stress, overload of metal ions including ferric, copper and zinc. Finally, the fibrils develop into extracellular deposits (senile plaques) of micron size in the progress of aging {12; 10; 13; 3; 14}. Although, it is controversial whether Aβ deposits precede and induce the neuronal atrophy {15} recent evidence indicates that Aβ plaques are the herald and critical mediator of neuritic pathology {2}.

Tau fibrils formation is another widely considered pathological hallmark for AD. They represent intracellular fibrils and tangles generated from helical parallel filament (HPF) protein {18; 19}. Although both Aβ plaques and tau fibrils are definite signs for AD, it is not yet clear whether Aβ plaques formation and Tau generation are linked to each other, or they exist as parallel pathological pathways {22; 30; 22; 21}.

Currently, the diagnosis of AD mainly relies on memory and behavior tests, and the final confirmation is usually based on postmortem analysis. Both memory and behavior tests, however, are not reliable and not suitable for the early detection because of the lack of noticeable syndrome at the early stage {20}. Therefore, the early detection of AD still presents a challenge. Molecular imaging, a molecular level and high sensitivity detecting technology, represents a promising approach to face this challenge. Molecular MR imaging, optical imaging and PET imaging have been employed as modalities for the early detection of AD pathology, and considerable progresses has been achieved in recent years {46; 24; 1; 7; 25; 27; 26; 110; 111; 112; 28}. Direct MRI visualization of Aβ plaques in AD brain tissue was reported, using MR microscopy and very long scanning time (24 hours) {26}. Targeting MRI detecting Aβ plaques with antibody conjugated with magnetic probes was also reported, but it required transient BBB opening {28}. Poduslo et al reported that a conjugate of gadolinium and modified Aβ40 segment (Aβ30) had BBB penetrating ability and was suitable for in vivo MRI visualization of Aβ plaques {27}.

In addition, Higuchi et al claimed that by using an Aβ plaque specific small molecular probe with fluoride, they were able to detect the deposit in transgenic mice by $^{1}$H MRI and $^{19}$F MRI {25}. Although these studies indicate that molecular MRI is a promising diagnostic modality, its low sensitivity could be an obstacle for its application in clinic. In recent years, researches have demonstrated that PET can be used as an imaging modality to detect AD pathology; however, its high cost and narrow availability of contrast agents prevent its broad usage {23}. Molecular optical imaging is a promising modality for early AD pathological detection. Multiphoton and near infrared imaging are the most used optical imaging modalities, based on the fluorescent property of the probes. Although multiphoton microscopy could be very useful in animal research, it is invasive and only provides very small field-of-view information {23; 7; 5; 6; 8}.

Near Infrared Imaging (NIR) is a very attractive tool for early AD detection because of its acceptable depth penetration, non-invasive operation, and inexpensive instrumentation. Several non-NIR molecules that specifically bind to senile plaques have been reported for multiphoton imaging and histological studies; near-infrared probes, however, are few {24; 3}. NIAD-4 was reported as a potential senile plaque-specific two-photon microscopy probe that could be used as a NIR probe. Most importantly, it showed significant fluorescence intensity increase upon binding to Aβ aggregates in in vitro test. Therefore, this type of molecule could be referred as a "smart" probe. NIAD-4 and its analogues are currently under investigation for senile plaque monitoring by measuring life time change {7; 3} Additionally, Chang et al reported that some styryl dyes could be "turned on" upon incubating with Aβ aggregates, but these compounds may have little chance penetrating BBB because of their large polarity {29}.

Curcumin, a brightly colored powder, is the principal curcuminoid of the Indian curry spice turmeric, and consumed daily for thousand of years in India and other regions. Curcumin is known for its antitumor, antioxidant, antiarthritic and anti-inflammatory properties {30; 32; 31; 33}. It has been utilized as an anti-amyloid agent as well {5; 157}. In 2004, Yang et al reported that curcumin could be used as a histological staining reagent for senile plaques and showed that curcumin could decrease amyloid deposits in vivo {34}. Further, Garcia-Alloza et al. demonstrated by two-photon imaging, that curcumin could be visualized in vivo and could prevent the progress of amyloid plaque forming in APP/Tau transgenic mice model {5}. In addition, Ryu pointed out that curcumin derivatives were suitable for amyloid deposit monitoring by PET {35}. All of the studies showed that curcumin is very specific for amyloid plaque and displays high affinity binding for Aβ aggregates. However, curcumin is not practical for in vivo NIR imaging because of its short emission wavelength and low lipophilicity (log $P<2$){35}.

As can be appreciated, it would be desirable to obtain new imaging agents useful for the detection of amyloid-β plaques in human subjects. In particular, it is desirable to utilize near-infrared (NIR) imaging as a sensitive, low cost and non-invasive approach for the early detection of AD. To meet this objective, "smart" probes that can be "turned on" with emission in the NIR imaging window are highly sought after in the medical imaging field.

SUMMARY OF THE INVENTION

The inventors show herein that by modifying curcumin's structure it is possible to shift derivative compounds' emission wavelength to an ideal range for NIR imaging. Accordingly, the invention provides "smart" probes with significant fluorescence property changes upon binding. In addition, derivative compounds are provided having improved lipophilicity relative to curcumin.

In a first aspect, the invention provides in a compound having the formula $Ar^1$-L-$Ar^2$, wherein: (a) L is a divalent linking group comprising an alkenylene having 5 to 15 backbone carbon atoms, wherein at least two of the backbone carbon atoms form part of a carbonyl or secondary alcohol and $Ar^1$ and $Ar^2$ are each independently alkyl amine-substituted aryl or heteroaryl groups; or (b) L is a divalent linking group comprising an alkenylene having 5 to 15 backbone carbon atoms, wherein at least two of the backbone carbon atoms form part of a difluoroboronate ring; and $Ar^1$ and $Ar^2$ are each independently alkyl amine-substituted aryl or heteroaryl groups.

In certain preferred embodiments, the linker L is —CH═CH—(CO)—CH═C(OH)—CH═CH— or —CH═CH—(CO)—$CH_2$—C(O)—CH═CH—. As well, the aryl or heteroaryl groups $Ar^1$ and $Ar^2$ are independently selected from:

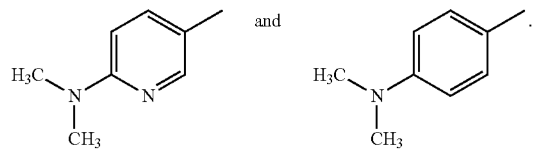

A particularly preferred compound of the invention has the structure:

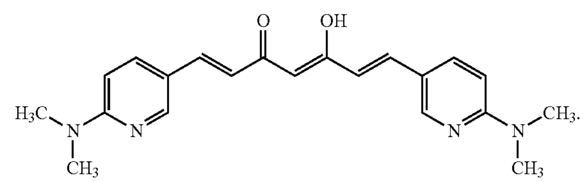 [SMILES: CN(C)c1ccc(/C=C/C(=O)/C=C(O)/C=C/c2ccc(N(C)C)nc2)cn1]

In other embodiments, the linker L is

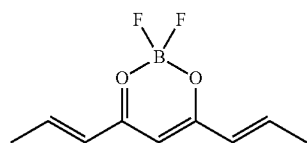

and, optionally, $Ar^1$ and $Ar^2$ are independently selected from

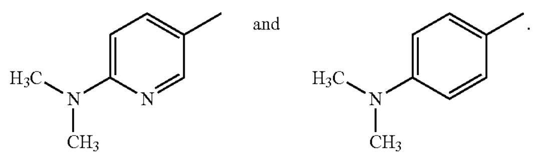

Yet another preferred compound according to the invention has the structure:

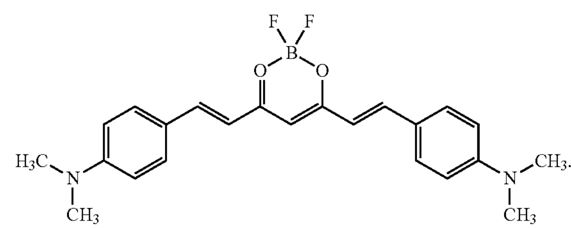

Compounds of the present invention are preferably capable of binding amyloid beta plaques in both in vivo and in vitro contexts.

In certain embodiments, the compounds of the invention are useful for imaging in other modalities in addition to near infrared (NIR). In such embodiments, the compounds are isotopically labeled with isotopes including, e.g., $^{18}F$ isotope, $^{19}F$ isotope, or $^{11}C$ isotope.

In another aspect, the invention provides a pharmaceutical injectable dosage formulated to include a compound as described and claimed herein and an injectable carrier system.

A further aspect of the invention is directed to a method for detecting an amyloid beta plaque in a sample. Such a method includes steps of: (a) contacting a sample comprising an amyloid beta plaque with a compound described and claimed herein such that the compound binds the amyloid beta plaque; (b) illuminating the compound bound to the amyloid beta plaque with near infrared light of a wavelength absorbable by the compound; and (c) detecting fluorescence emitted by the compound wherein the fluorescence corresponds to the amyloid beta plaque contained in the sample.

In certain embodiments, the presence, absence or level of said compound's fluorescence in the sample is indicative of a disease state, the disease state preferably being Alzheimer's disease.

In another aspect, the invention encompasses an in vivo optical imaging method for amyloid beta plaque detection. Such a method includes steps of: (a) administering to a subject a compound as described and claimed herein wherein the compound binds an amyloid beta plaque; (b) illuminating the subject with near infrared light of a wavelength absorbable by the compound; and (c) detecting fluorescence emitted by the compound wherein the fluorescence corresponds to the amyloid beta plaque present in the subject.

In certain embodiments, the fluorescence detected in step (c) is used in an additional step to construct an image of the amyloid beta plaque present in the subject.

The step (c) of the method is preferably performed using a light detection or image recording component comprising a charge coupled device (CCD) system or photographic film. As well, steps (b) and (c) are preferably performed using an endoscopic device, a catheter-based device, a diffuse optical tomographic imaging system, phased array technology, a confocal imaging system, or an intravital microscopy system.

In the method, the presence, absence or level of the compound's fluorescence is indicative of a disease state, preferably Alzheimer's disease.

In preferred methods, the subject is a living animal, most preferably a human subject.

The method typically accomplishes administration of the compound to the subject by intravenous (IV) injection.

In yet another aspect, the invention provides a method for providing a positron emission tomography (PET) scan of a subject. Such a method includes steps of: (a) administering to a subject a $^{11}C$ or $^{18}F$ labeled derivative of a compound described and claimed herein; and (b) imaging gamma rays emitted due to the compound within the subject in order to provide a PET scan of the compound contained in the subject. The presence, absence or level of the compound within the subject is typically indicative of a disease state, most preferably Alzheimer's disease.

The invention provides in a further aspect a method for providing a magnetic resonance image of a subject. Such a method includes steps of: (a) administering to a subject a $^{19}F$ labeled derivative of a compound described and claimed herein; and (b) imaging the subject in order to obtain a magnetic resonance image of the compound contained within the subject. The presence, absence or level of the compound within the subject is typically indicative of a disease state, most preferably Alzheimer's disease.

The invention further encompasses an optical system for imaging an amyloid beta plaque in a subject. Such a system includes: (a) a fluorescence excitation source for illuminating at least a portion of the subject, the fluorescence excitation source configured to excite fluorescent emission of a compound described and claimed herein that is administered to the subject to bind amyloid beta plaque present in the subject; (b) a fluorescence light detector for detecting fluorescent light emitted by the compound; and (c) an imaging means to provide an image of the compound in the subject which correlates to amyloid beta plaque present in the subject.

The fluorescence excitation source in the system may be a laser or light-emitting diode.

The fluorescence light detector in the system may be a charge coupled device (CCD) system or photographic film.

In certain embodiments, the fluorescence excitation source and the fluorescence light detector are embodied in an endoscopic device, a catheter-based device, a diffuse optical tomographic imaging device, a phased array technology device, a confocal imaging device, or an intravital microscopy device.

Of course, the invention also contemplates the use of a compound as described and claimed herein for the manufacture of an injectable dosage for the in vivo imaging of a subject as well as the use of the present compounds in in vivo imaging of a subject.

Other objects, features and advantages of the present invention will become apparent after review of the specification, claims and drawings.

DETAILED DESCRIPTION OF THE INVENTION

I. In General

Figure 1:
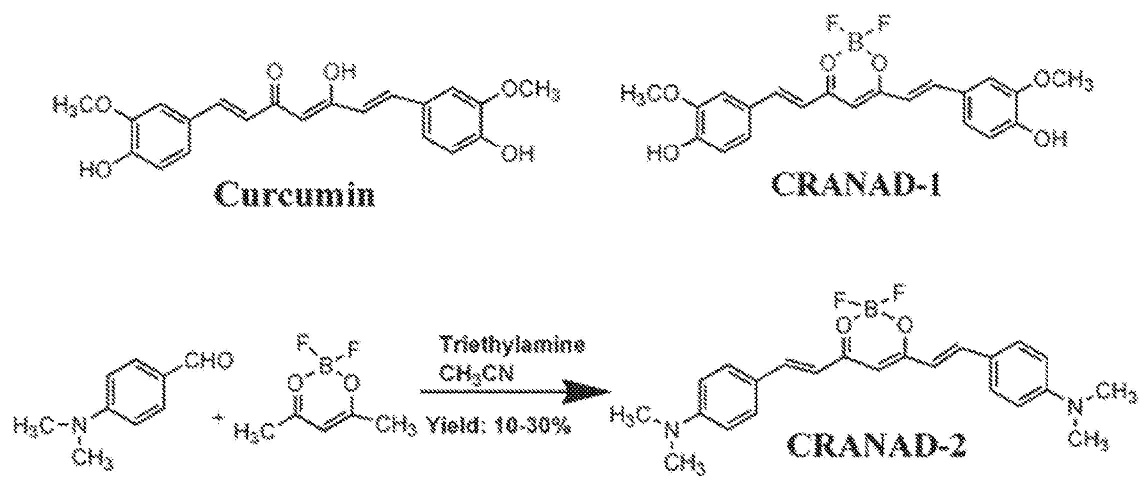
FIG. 1. The structure of Curcumin, CRANAD-1 (Top), CRANAD-2, and the synthetic route of CRANAD-2 (bottom).

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed nonprovisional applications.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising" and variations thereof do not have a limiting meaning where these terms appear in the description and claims. Accordingly, the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The terminology as set forth herein is for description of the embodiments only and should not be construed as limiting of the invention as a whole. Unless otherwise specified, "a," "an," "the," and "at least one" are used interchangeably and mean one or more than one.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for curcumin derivatives of this invention are those that do not interfere with the curcumin derivatives imaging activity. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

The term "heterocyclic" includes cycloalkyl or cycloalkenyl non-aromatic rings or ring systems that contain at least one ring heteroatom (e.g., O, S, N).

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are difluoromethyl, trifluoromethyl, and the like. Halogens are elements including chlorine, bromine, fluorine, and iodine.

The term "aryl" as used herein includes monocyclic or polycyclic aromatic hydrocarbons or ring systems. Examples of aryl groups include phenyl, naphthyl, biphenyl, fluorenyl and indenyl. Aryl groups may be substituted or unsubstituted. Aryl groups include aromatic annulenes, fused aryl groups, and heteroaryl groups. Aryl groups are also referred to herein as aryl rings.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The terms "arylene" and "heteroarylene" are the divalent forms of the "aryl" and "heteroaryl" groups defined above. The terms "arylenyl" and "heteroarylenyl" are used when "arylene" and "heteroarylene", respectively, are substituted. For example, an alkylarylenyl group comprises an arylene moiety to which an alkyl group is attached.

The term "fused aryl ring" includes fused carbocyclic aromatic rings or ring systems. Examples of fused aryl rings include benzo, naphtho, fluoreno, and indeno.

The term "annulene" refers to aryl groups that are completely conjugated monocyclic hydrocarbons. Examples of annulenes include cyclobutadiene, benzene, and cyclooctatetraene Annulenes present in an aryl group will typically have one or more hydrogen atoms substituted with other atoms such as carbon.

When a group is present more than once in any formula or scheme described herein, each group (or substituent) is independently selected, whether explicitly stated or not. For example, for the formula —$C(O)NR_2$ each of the two R groups is independently selected.

As a means of simplifying the discussion and the recitation of certain terminology used throughout this application, the terms "group" and "moiety" are used to differentiate between chemical species that allow for substitution or that may be substituted and those that, in the particular embodiment of the invention, do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The invention is inclusive of the compounds described herein (including intermediates) in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

"Pharmaceutically acceptable" as used herein means that the compound or composition or carrier is suitable for administration to a subject to achieve the treatments described herein, without unduly deleterious side effects in light of the necessity of the treatment.

II. The Invention

As noted above, curcumin (diferuloylmethane, 1,7-bis(4-hydroxy-3-methoxyphenyl)-1,6-heptadiene-3,5-dione) is a symmetrical diphenolic dienone. It exists in solution as an equilibrium mixture of the symmetrical dienone (diketo) and the keto-enol tautomer; the keto-enol form is strongly favored by intramolecular hydrogen bonding.

Curcumin contains two aryl rings separated by an unsaturated seven carbon spacer having two carbonyls. The aryl rings of curcumin contain a hydroxyl group in the para position and a methoxy group in the meta position.

In this invention, the inventors provide the design, synthesis and testing of a family of novel "smart" NIR Aβ plaque-specific fluorescent probes which open a wide window for new types of NIR fluorescent dyes for cell, tissue, and in vivo imaging.

In one particular embodiment, a probe according to the invention was designed by incorporating a difluoroborate ring into curcumin (FIG. 1; hereafter "CRANAD-2"). This probe is the first example of difluoroborate diketone family as imaging probe. This particular probe, exemplary of the invention, is an ideal NIR probe for detecting Aβ aggregates. First, the probe has a molecular weight is only 400 dalton. Its log P is 3.0, which is within the range for the recommended lipophilicity (log p 2-5) for CNS drugs that have high potential to penetrate brain blood barrier. Second, utilizing a two-step red-pushing strategy, the inventors obtained the compound with fluorescence emission that falls into the ideal "optical window" (650-900 nm) for NIR imaging.

At the same time CRANAD-2 also exhibits a large stoke shift (140 nm in PBS, and 70 nm in PBS with Aβ aggregates). Moreover, CRANAD-2 shows high quantum yield upon binding to aggregates (40%) though its quantum yield was low (0.6%) in PBS buffer. Third, CRANAD-2 exhibits considerable stability in serum in vitro, which was further confirmed in the inventor's in vivo studies. Additionally, CRANAD-2 does not show any significant binding to BSA, the major serum protein component. Fourth, CRANAD-2 possesses high affinity to Aβ aggregates, with the $K_d$ comparable to that of Thioflavin T and NIAD-4, and being significantly higher than AOI 987. Fifth, CRANAD-2 displays specific staining with Aβ plaques from aged transgenic mice brain tissue, indicating that the probe has particular selectivity for Aβ plaques over other components of brain tissue. Sixth, CRANAD-2 displays specific properties of a "smart" probe since its emission wavelength and fluorescence intensity and lifetime were highly sensitive to the binding with Aβ plaques. After binding to Aβ plaques, the probe was "turned on" and displayed 70 folds increase in fluorescence intensity and 90 nm blue-shift, and significant lifetime change upon binding to the aggregates. The term "fluorescence properties" refer to fluorescence intensity properties; the probe will be "turn on" upon interacting with a target, exhibiting "smart" probe properties, or significant fluorescence life time shortening or prolonging. Finally, the inventors demonstrated that CRANAD-2 could be used for early AD detection in an animal model.

In use, the CRANAD-2 probe of the present invention may be used for several purposes. For instance, the described probe is a potential research tool for animal studies; a diagnosis agent for clinic in the future; a fluorescent dye for biology studies; a potential class of drugs to treat AD; a potential MRI imaging probe for AD diagnosis (e.g., CRANAD-2 containing at least one fluorine atom which is an $^{19}F$ isotope); and a potential PET probe for AD diagnosis (e.g., CRANAD-2 containing at least one fluorine atom which is an $^{18}F$ isotope or, alternatively, at least one carbon atom which is a $^{11}C$ isotope).

Curcumin derivatives are expected to be beneficial for use in the imaging methods of the invention. The term "curcumin derivative" is used interchangeably with the term "curcumin analog" and "curcumin analogue" (alternative spelling) and includes, for example, curcumin derivatives, analogs, curcuminoids and chalcones. In one embodiment, the curcumin derivative includes first and second aryl groups covalently attached by way of a spacer, also referred to herein as a linker or a linking group. In another embodiment, the first and/or second aryl group is a heteroaryl group.

Curcumin derivatives that exhibit improved imaging qualities are preferred. For example, curcumin derivatives that include alkyl amine-substituted aryl or heteroaryl groups and unsaturated spacers are expected to impart improved imaging characteristics. Additional curcumin derivatives not encompassed by the general definition provided above may also be found in the examples and schemes provided herein.

Curcumin derivatives of the invention are generally encompassed by compounds having the formula $Ar^1$-L-$Ar^2$, wherein: (a) L is a divalent linking group comprising an alkenylene having 5 to 15 backbone carbon atoms, wherein at least two of the backbone carbon atoms form part of a carbonyl or secondary alcohol and $Ar^1$ and $Ar^2$ are each independently alkyl amine-substituted aryl or heteroaryl groups; or (b) L is a divalent linking group comprising an alkenylene having 5 to 15 backbone carbon atoms, wherein at least two of the backbone carbon atoms form part of a difluoroboronate ring; and $Ar^1$ and $Ar^2$ are each independently alkyl amine-substituted aryl or heteroaryl groups.

Curcumin derivatives of the invention include aryl or heteroaryl group $Ar^1$, which is positioned at an end of the linker L. Curcumin derivatives of the invention include a second aryl or heteroaryl group $Ar^2$ that is independently selected from $Ar^1$, which is positioned at the other end of the linker L. Preferred aryl or heteroaryl groups include phenyl groups, naphthyl groups, thienyl groups, and pyridinium groups.

Aryl or heteroaryl groups $Ar^1$ and $Ar^2$ are preferably substituted with an amine group, more preferably an alkyl amine group. Additional substituents may be present on the aryl or heteroaryl groups, wherein the ring positions may, independently, be unsubstituted (i.e., R=hydrogen) or one or more R groups may be substituents independently selected from a variety of substituents, including hydroxyl, halogen, alkyl, alkenyl, haloalkyl, alkoxy, amine, carboxyl, and ester substituents. Particularly preferred groups for $Ar^1$ and $Ar^2$ include:

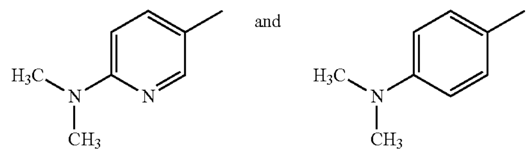

The linker L is a spacer preferably 5-15 carbon atoms in length that form a linear carbon chain connecting the first and second Ar groups. The carbons atoms in the carbon chain that trace out shortest path between the first and second Ar groups are referred to herein as the "backbone" carbon atoms. The number of backbone carbon atoms is readily determined in straight chain alkyl groups. In spacers that include a cyclic alkyl group as a constituent of the linear chain, the backbone carbon atoms include the least number of ring carbons possible. The number of backbone carbon atoms is used herein as a shorthand way to designate the length of the linker being used. For example, a 7-carbon spacer is a divalent spacer that includes 7 backbone carbon atoms. Preferred embodiments of the invention include curcumin derivatives having an odd number of carbon atoms; e.g., 3, 5, and 7-carbon linking groups.

In certain embodiments of the invention, at least one of the backbone carbon atoms is included in a carbonyl (C═O) moiety. The spacer may be substituted or unsubstituted. The spacer may further be saturated or unsaturated. In a preferred embodiment, the spacer contains an odd number of carbon atoms (i.e., 3, 5, or 7 carbon atoms), and alternating unsaturated carbon-carbon bonds. In additional embodiments, the spacer may include a hydroxyl moiety in place of, or in addition to, the at least one carbonyl moiety. Particularly preferred spacers include —CH═CH—(CO)—CH═C(OH)—CH═CH— or —CH═CH—(CO)—$CH_2$—C(O)—CH═CH—. In other embodiments, at least two carbons of the linker's backbone are involved in forming a difluoroboronate ring structure. A particularly preferred linker of this type is illustrated by the structure:

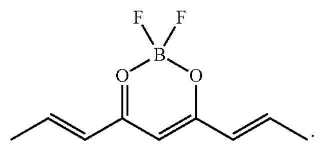

As can be appreciated, curcumin derivatives of the invention preferably include a linking group L that includes an alkenylene group having between 3 and 7 backbone carbon atoms and preferably at least one carbonyl moiety. The linking group may be substituted or unsubstituted, and may be saturated or unsaturated. Preferably, an unsaturated linking group includes conjugated double bonds. Preferably the linking group also contains an odd number of carbon atoms (i.e., 3, 5, or 7 carbon atoms), and at least one unsaturated carbon-carbon bond. In additional embodiments, the linking group may include a hydroxyl moiety in place of, or in addition to, the at least one carbonyl moiety.

A divalent linking group includes two carbons with unfilled valencies that provide valence points where a covalent bond can be formed to an adjacent aryl or heteroaryl group that also includes a carbon with an unfilled valency. Generally, a valence point is represented in a chemical formula by a bond that is shown as not being attached to another group (e.g., $CH_3$—, wherein — represents the valence point).

To further describe and illustrate exemplary compounds of the present invention, various curcumin derivatives of the invention may be represented by the general formula (I):

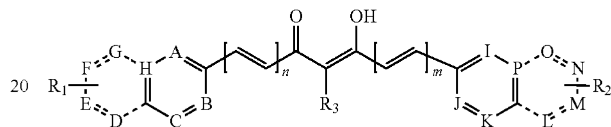

wherein positions A, B, C, D, E, F, G, H, I, J, K, L, M, N, O, and P are independently selected from the atoms C, N, O, or S; n and m are independently 1, 2, or 3; R1 and R2 are each an alkyl amine substituted group; and R3 is an alkyl, $N(R_4R_5)$, $OR_6$, fluoroalkyl, $N(R_4)(CH_2)nOR_7$, $N(R_4)(CH_2)nOR_7$, $N(R_4)(CH_2)n^{18}F$, $N(R_4)(CH_2)_nN(R_8R_9)$; $N^{11}CH_3R_{10}$ (where $R_4$, $R_5$, $R_6$, $R_7$, $R_8$, $R_9$, $R_{10}$ is an alkyl group).

As well, other exemplary curcumin derivatives of the invention are represented by the general formula (II):

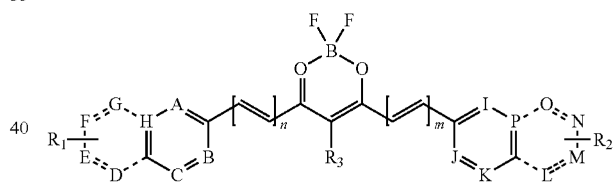

wherein positions A, B, C, D, E, F, G, H, I, J, K, L, M, N, O, and P are independently C, N, O, or S: n and m are independently 1, 2, or 3: R1, R2, are each an alkyl amine substituted group; and R3 is an alkyl, $N(R_4R_5)$, $OR_6$, fluoroalkyl, $N(R_4)(CH_2)nOR_7$, $N(R_4)(CH_2)nOR_7$, $N(R_4)(CH_2)n^{18}F$, $N(R_4)(CH_2)_nN(R_8R_9)$; $N_{11}CH_3R_{10}$ (where $R_4$, $R_5$, $R_6$, $R_7$, $R_5$, $R_9$, $R_{10}$ is an alkyl group).

Particularly preferred compounds according to the invention having demonstrated advantage as "smart" NIR probes include compounds defined by the structures:

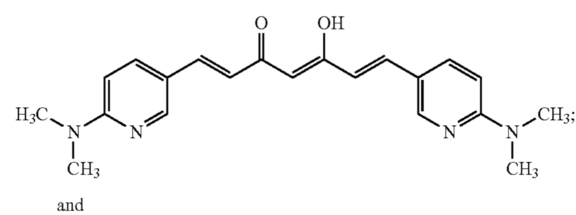

and

-continued

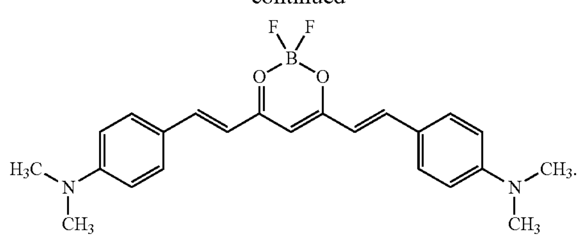

In certain embodiments, the invention provides compounds that are further useful in modalities other than NIR such as positron emission tomography (PET) or magnetic resonance imaging (MRI). The general formula (III) below illustrates various examples of isotopically-labeled derivatives of the present compounds labeled with the isotopes $^{11}C$, $^{18}F$ (for use in PET) or $^{19}F$ (for use in MRI).

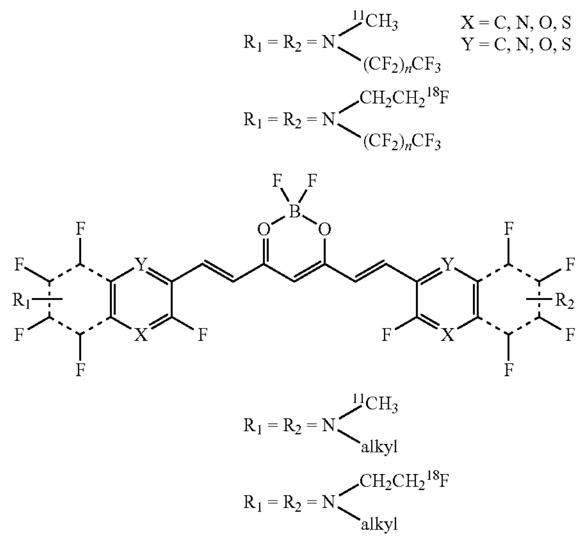

Methods of providing isotopically labeled molecules are well know in the art and the artisan may resort to a variety of known methods to derive isotopically labeled versions of the compounds described and claimed herein. (e.g., see Ryu et al., *J. Med. Chem.* 2006, 6111-6119; Cai et al., *Current Medicinal Chemistry,* 2007, 14, 19-52; and Ametamey et al., *Chem. Rev.,* 2008, 108, 1501-1516.) Accordingly, all isotopically labeled versions of the present compounds accessible through routine labeling procedures are encompassed within the present invention.

Specific methods to synthesize compounds according to the invention are set forth below in the Examples section. Stated generally, compounds of the invention are accessible via the following reaction scheme and general set of reagents:

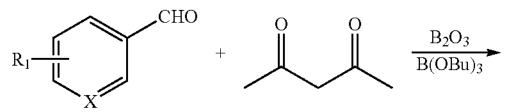

-continued

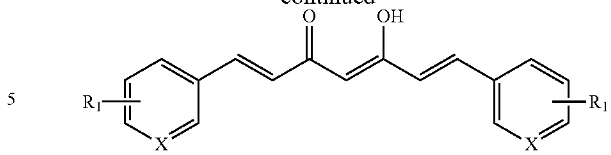

For example, the compound CRANAD-5 is provided where X is carbon and $R_1$ is the group —$N(CH_3)_2$. In similar fashion, the compound CRANAD-3 is achieved where X is nitrogen and $R_1$ is the —$N(CH_3)_2$ group.

The compounds of the present invention are particularly useful when formulated in the form of a pharmaceutical injectable dosage, including a compound described and claimed herein in combination with an injectable carrier system. As used herein, injectable and infusion dosage forms (i.e., parenteral dosage forms) include, but are not limited to, liposomal injectables or a lipid bilayer vesicle having phospholipids that encapsulate an active drug substance. Injection includes a sterile preparation intended for parenteral use.

Five distinct classes of injections exist as defined by the USP: emulsions, lipids, powders, solutions and suspensions. Emulsion injection includes an emulsion comprising a sterile, pyrogen-free preparation intended to be administered parenterally. Lipid complex and powder for solution injection are sterile preparations intended for reconstitution to form a solution for parenteral use. Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization. Solution injection involves a liquid preparation containing one or more drug substances dissolved in a suitable solvent or mixture of mutually miscible solvents that is suitable for injection. Solution concentrate injection involves a sterile preparation for parenteral use that, upon addition of suitable solvents, yields a solution conforming in all respects to the requirements for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

The tolerable dosage for administration to animals, including humans, is from about 0.001 mg/kg to about 40 mg/kg. Specifically, for NIR imaging, the preferable dosage is from about 1.0 mg/kg to about 10.0 mg/kg; for PET imaging, the dosage is from about 0.001 mg/kg to about 0.1 mg/kg; for MRI imaging, the dosage is from about 1.0 mg/kg to about 40 mg/kg. Based on these parameters, the artisan may perform no more than routine experimentation to optimize adjust the dosage for a particular application.

In yet other embodiments, the invention encompasses optical systems for imaging amyloid beta plaque in a subject via the NIR modality. Such systems include: (a) a fluorescence excitation source for illuminating at least a portion of the subject, the fluorescence excitation source configured to excite fluorescent emission of a compound described and claimed herein that is administered to the subject to bind amyloid beta plaque present in said subject; (b) a fluorescence light detector for detecting fluorescent light emitted by the compound; and (c) an imaging means to provide an image of the compound in the subject which correlates to amyloid beta plaque present in the subject.

Suitable fluorescence excitation sources include, e.g., a laser or light-emitting diode. As well, suitable fluorescence light detectors may be in the form of, e.g., a charge coupled device (CCD) system or photographic film. In certain embodiments, the fluorescence excitation source and the fluorescence light detector are embodied in an endoscopic device, a catheter-based device, a diffuse optical tomographic imaging device, a phased array technology device, a confocal imaging device, or an intravital microscopy device.

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

Example 1

Methods and Materials.

Reagents used for synthesis were purchased from Aldrich without further purification. Column chromatography was performed on silica gel (SiliCycle Inc., 60 Å, 40-63 mm) slurry packed into glass columns. Thioflavin S was purchased from Aldrich. Synthetic amyloid-b protein (1-40) was purchased from rPeptide (Bogart, Ga., 30622) and aggregates for in vitro studies were generated followed the reported procedure. BSA was purchased from Sigma, and human serum was obtained from Invitrogen (type AB). $^{1}$H and $^{13}$C NMR spectra were recorded at 400 MHz and 100 MHz respectively, and are reported in ppm downfield from tetramethylsilane. Fluorescence studies were carried out with F-4500 Fluorescense Spectrophotometer. Fluorescence quantum yields were determined using aqueous solution of Cy5.5-maleimide as a standard (y=0.23). High resolution mass spectra were obtained at the Harvard University, Department of Chemistry Instrumentation Facility. Transgenic Tg2576 mice {45} and littermates were purchased from Taconic Farm, Balb/c mice for BBB penetrating test were obtained from Jackson Laboratory, and the experiment procedure was approved by Massachusetts General Hospital. In vivo imaging was recorded on Kodak Imaging Station 2000MM.

Synthesis of CRANAD-1 and CRANAD-2.

The synthesis of CRANAD-1 was performed according to the reported procedure {41}. Synthesis of CRANAD-2 (2,2-difluoro-1,3-dioxaboryl-pentadione) was performed according to the following procedure: 1,3-pentadione (0.1 g, 1.0 mmol) and trifluoroboron ether (0.2 g, 1.0 mmol) were mixed together, and the resulting solution was heated at 60° C. for 2 h. After cooling to the room temperature, the reaction mixture was subjected to evaporation under vacuum, and yellow pale semisolid was obtained, which was solidified with longer standing at room temperature to give a yellow pale needle crystal. The above crystals (0.15 g, 0.1 mmol) were dissolved in acetonitrile (3.0 ml). To the above solution, triethylamine (0.30 g, 3.0 mmol) was added, followed by the addition of 4-N,N-dimethyl-benzaldehyde (0.30 g, 2.0 mmol). The resultant was stirred at 60° C. overnight. After removing the solvent a black residue was obtained, and subjected to flash column chromatography with methylene chloride to give black powder (63.0 mg, yield: 15%). $^{1}$H NMR (DMSO-d6) δ(ppm) 3.04 (s, 12H), 6.26 (s, 1H), 6.79 (m, 6H), 7.68 (d, 4H, J=8.0 Hz), 7.82 (d, 2H, J=16 Hz); $^{13}$C NMR (DMSO-d6) δ(ppm) 40.3, 100.6, 112.1, 113.3, 121.8, 132.3, 150.3, 153.5; $^{19}$F NMR (DMSO-d6) δ(ppm) −138.9.

Log p Measurement.

Log p measurement was performed according to the reported procedure {35}. CRANAD-2 (0.125 mM) in Octanol 2.0 mL was subjected to partition with octanol-saturated water 2.0 mL. The resulting mixture was stirred vigorously for 5 min., and centrifuged at 2,000 rpm for 5 min. The octanol layer was separated from water layer, and its fluorescence spectrum was recorded (excited at 590 nm). The above water layer was partitioned with water-saturated octanol 2.0 mL, and the octanol layer was separated after 5 min. vigorous stirring and 5 min. centrifuge at 2,000 rpm, and its spectrum was recorded. The log P value was calculated by the fluorescence intensity ratio at 690 nm for the above two octanol extractions.

In Vitro Aβ Aggregates Binding Constant Measurement.

To PBS solutions (1.0 mL) of Aβ40 aggregates (5.004, calculation based on Aβ40 peptide concentration), various amounts of CRANAD-2 were added to the final concentration of 2.5, 5.0, 10.0, 20.0, 40.0, 60.0, 100.0 150.0, 200.0, 250.0, 300.0 nM, and their fluorescence intensities at 715 nm were recorded (Ex: 640 nm). The Kd binding curve was generated by software Prism 3.0 with nonlinear one-site binding regression. By measuring the fluorescence intensity of CRANAD-2 alone in PBS buffer (50.0, 100.0, 350.0, 850.0, 1200.0 nM), we confirmed that there was no self-quenching of the dye within the range of the above tested concentrations.

Serum Stability Test.

CRANAD-2 (4.0 μM) was incubated at 37° C. for 2 h with 1.0 mL human serum, then ethyl acetate (4×5.0 mL) was added, stirred at room temperature for 10 min., and centrifuged to give clear organic supernatant. The ethyl acetate solution was subjected to fluorescence intensity measurement (F.I.(660 nm)=8713), and the concentration of CRANAD-2 was calculated (0.14 μM) using the equation (Y=474+61.7 X, where Y is F.I., and X is the concentration) generated from standard curve of CRANAD-2 in ethyl acetate. The recovery of CRANAD-2 was about 70%. After the fluorescence measurement, the ethyl acetate solution was concentrated to 40 μL, and 10 μL was injected for HPLC analysis. By HPLC, the recovery of CRANAD-2 was about 75%, which was close to the result from fluorescence measurement.

BSA Interaction with CRANAD-2.

CRANAD-2 was added to a BSA (20 μg/mL) solution to make the final concentration of 5 μM. The fluorescence spectrum of the above mixture was recorded (excited at 590 nm). For comparisons, CRANAD-2 (5 μM) in PBS, PBS alone, and Aβ40 aggregates (20 m/mL) and CRANAD-2 (5 μM) were prepared.

Histological Evaluation.

Tg2576 mice brain tissue was cut into 25 micron slices. The slices were fixed with 4% formalin for 5 min and washed with PBS buffer twice. For Thioflavin S staining the slices were dipped into thioflavin S solution (1.0% in 50% ethanol) for 5 min., then differentiated in 70% ethanol for 5 min., rinsed with distilled water twice and mounted using Vecta shield mounting medium. Similar procedure was used to incubate sliced tissue with our probe. Histological slide was treated with, 0.01% CRANAD-2 in 10% acetone, 40% ethanol and 50% water for 15 min. For co-staining: the procedure was similar. The slices were first stained with thioflavin S, and washed with 70% ethanol for 5 min, then stained with the solution of CRANAD-2.

BBB Penetration.

To test the BBB penetrating ability of the probe, Balb/c mice were used (n=3). Mice were intravenously injected with CRANAD-1 probe (10.0 mg/kg, 20% DMSO and 80% propylene glycol). Mice were perfused with saline solution and the brains were excised at 30 min., 1 h, 2 h, and 4 h after injection. Each brain sample was homogenized with 2.0 ml water and 3.0 ml ethyl acetate, and the homogenate was centrifuged for 5 min at 2,500 rpm. The fluorescence intensities of the ethyl acetate supernatant were recorded. The actual amounts (pmol) of the extracted probe were calculated according to the standard curve of CRANAD-2 in ethyl acetate.

Prior to perfusion, blood samples were taken at each time point to monitor the probe blood clearance. The blood samples were diluted with PBS buffer to 1.0 mL, followed by ethyl acetate (2.0 mL) extraction. The extractions were subjected to fluorescence intensity measurement, and the actual amounts of the probe for each mouse were calculated as the procedure for brain extraction described above.

In Vivo Imaging: NIR Imaging.

In vivo NIR imaging was performed using Kodak Imaging station 2000MM. For fluorescence excitation, three laser diodes at 660 nm with a total power of 10 mW/cm2 have been used yielding a uniform illumination of the whole animal. The fluorescent light emitted from the sample (mouse) was detected by a charge-coupled device (CCD) camera (Hamamatsu ORCA) equipped with a focusing lens system (macro lens 60 mm, 1:2.8, Nikon). The image matrix comprised of 532×256 pixels. A bandpass filter was used for the selection of the detection wavelength (700 nm). Integration time default was selected at 30 s. Images were acquired Kodak 1DTM 3.6.3 Network software and analysed using the Kodak™ 1D Analysis software.

Mice (n=3 for Tg2576 and n=3 for the littermates) were shaved before background imaging, and were i.v. injected CRANAD-2 (5.0 mg/kg) for each mouse. Fluorescence signals from the brain were recorded at pre-injection, and 10 min., 30 min., 60 min., 120 min., 240 min., and 480 min. after intravenous injection of the probe. To evaluate our imaging results, an ROI was drawn around the brain region, and the data were analyzed by the following modified equation (1) {24}, where Irel(t) is the relative fluorescence intensity at the certain time point, I(t) is the measured ROI value at this time point, I(pre) is the pre-injection background, and I(30) is the reading at 30 min. Since pre-injection background varied in different mice, this equation allowed us to correct for it. Fluorescence intensity decay curves were then generated based on this equation.

$$I\text{rel}(t)=(I(t)-I(\text{pre}))/(I(30)-I(\text{pre})) \quad (1)$$

For in vivo specific binding (SP), the calculation was based on equation (2), where Irel(tg) is the relative fluorescence intensity of Tg2576, and Irel(contr) is the relative fluorescence intensity of the control littermates. P values were calculated by Student test.

$$\text{SP}(t)=\{I\text{rel}(tg)-I\text{rel}(\text{contr})\}/I\text{rel}(tg) \quad (2)$$

Ex Vivo Histological Correlation.

19 month-old mouse was injected CRANAD-2 (10.0 mg/kg), and was sacrified after perfusion with 4% formaldehyde. The brain was taken and embedded in OCT. For histology, the brain was sliced into 25μ slices, and co-stained with thioflavin S as described above.

Probe Design, Synthesis, and Properties.

The rationale behind the design of the NIR probe of the present invention was based on three observations. First, it is a well known fact that curcumin reacts with boric acid to form a red colored compound rosocyanine, which consists of two curcumins connected by a borate ring {37; 36}. The color change from yellow (curcumin) to red (rosocyanine), however, points toward a possible UV red shift, which may be ascribed to the contribution of n→π (from oxygen to empty orbital of boron) of the borate ring of rosocyanine. Therefore, the inventors attempted to design boron contained curcumin derivatives with the emission shifted towards 650-900 nm range. Second, based on the previous studies with cyanine-like boron diketonates (2,2-difluoro-1,3,2-dioxaborines, {39; 40}), the inventors speculated that the emission of curcumin derivatives could produce an appropriate red shift by incorporating difluoro-boronate moiety into curcumin. Finally, based on the fact that N,N'-dimethyl group is well-known as the best UV red-shift pushing group for para-substituted aromatic ring, we further modified curcumin by replacing the phenolic hydroxyl group with N,N'-dimethyl group (FIG. 1).

Therefore, based on the above facts, probe 1 and probe 2 were designed and synthesized. Compound 1 (1,7-Bis-(4-hydroxy-3-methoxyphenyl)-hepta-1,6-diene-2',2'-difluoro-1',3'-dioxaboryl-3,5-dione) is known, and has been previously tested for HIV-1 and HIV-2 protease inhibitory activity {42} This probe was synthesized by following the reported procedure {41; 42} while compound 2 was prepared by condensation of 4-N,N'-dimethylbenzaldehyde with 2,2-difluoro-1,3-dioxaboryl-pentadione in acetonitrile {40}. For convenience, in the proceeding of this report, we named compound 1 as CRANAD-1, and compound 2 as CRANAD-2.

Figure 2:
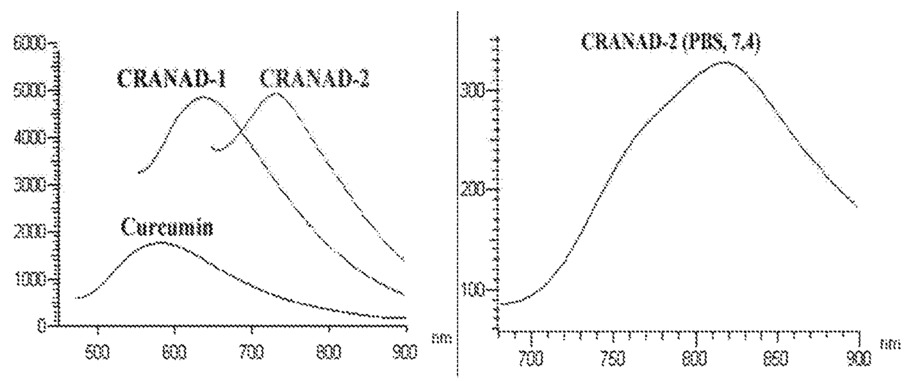
FIG. 2. The emission comparison between curcumin, CRANAD-1 and CRANAD-2 (2.5 μM) in methanol (left); and the emission spectrum of CRANAD-2 (2.5 μM) in PBS (pH 7.4) (right).

As anticipated, there was about 80 nm red shift of emission after installation of the difluoro-boron ring into curcumin molecule (CRANAD-1). The maximum emission of CRANAD-1 was 640 nm, while the λmax(em) of curcumin was 560 nm. There was also a 100 nm stokes shift for CRANAD-1 (λmax(ex)=540 nm, λmax(em)=640 nm), which was larger than that of curcumin's 50 nm (λmax(ex)=510 nm, λmax(em)=560 nm) (FIG. 2). However, while the inventors achieved considerable red shift and stokes shift from CRANAD-1, the ultimate goal was to push the emission further into NIR range. To do that, the inventors further modified CRANAD-1 by replacing the phenolic hydroxyl group with N,N'-dimethyl group to yield compound CRANAD-2.

Figure 3:
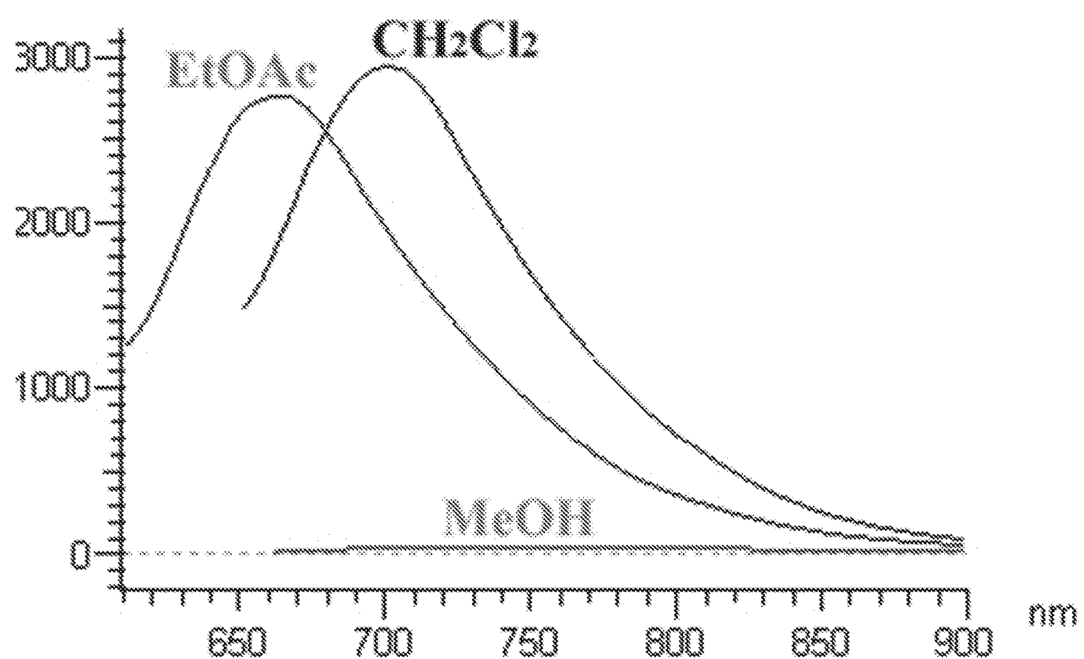
FIG. 3. The solvent-dependent emission of CRANAD-2 (25.0 μM) in dichloromethane, ethyl acetate, and methanol.
Figure 4:
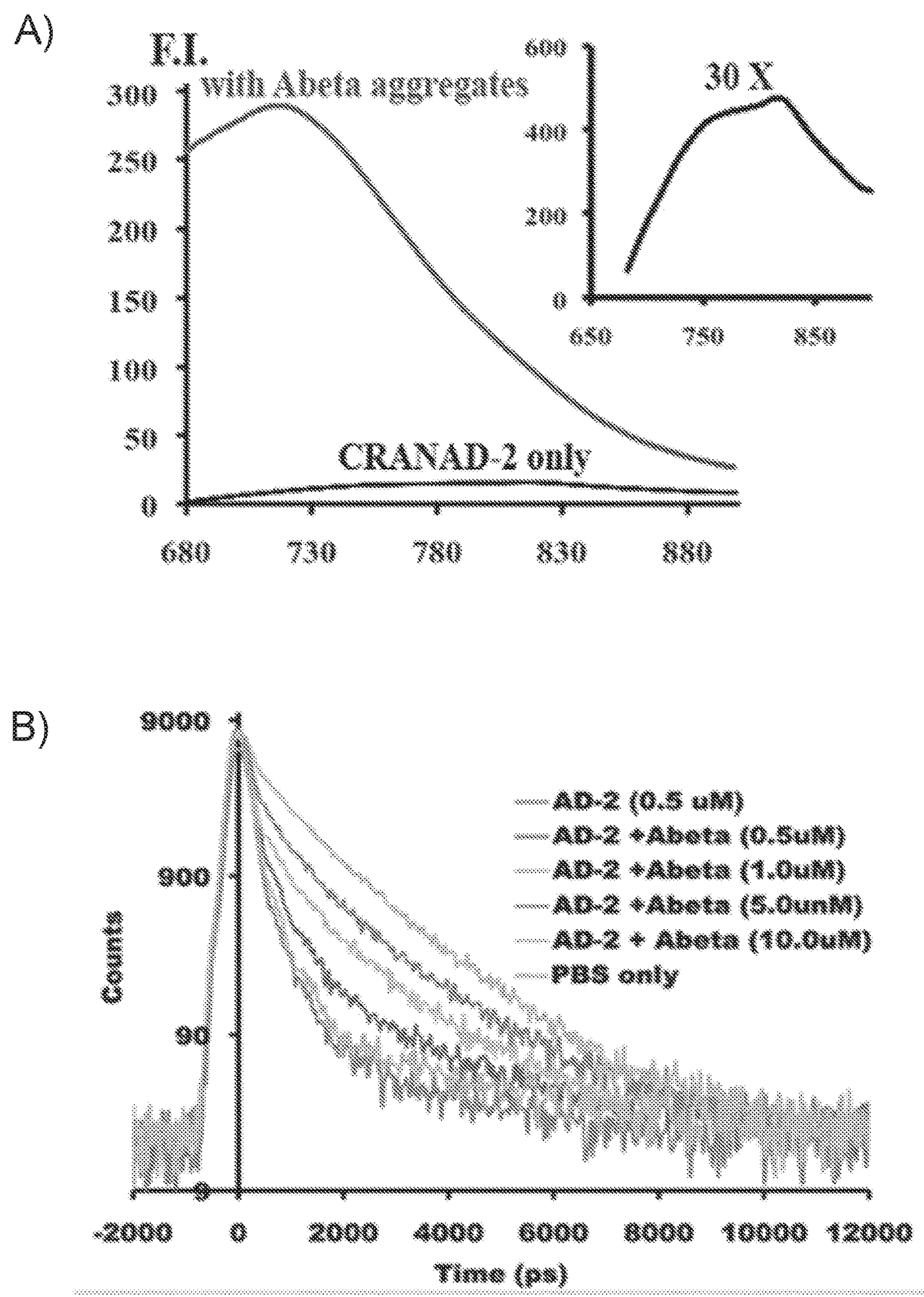
FIG. 4. a) The fluorescence switch of CRANAD-2 (100 nM) induced by by Aβ aggregates (blue line), Aβ40 monomer (pink line), and PBS only (yellow line). b) the lifetime change of CRANAD-2 after its binding to the aggregates (upper line: with aggregates; lower line: probe alone).

Indeed, by this replacement, the emission of compound CRANAD-2 was red-shifted to λmax(em)=760 nm, which fell in the best range for NIR probes. The compound also displayed a large stokes shift (λmax(ex)=640 nm, λmax(em)=760 nm) (FIG. 4). Furthermore, by comparing the fluorescence intensity in methanol, the quantum yield of CRANAD-2 was significant higher than that of curcumin (FIG. 2). As expected, the emission wavelength of CRANAD-2 displayed a typical solvent-dependency (FIG. 3), i.e., it showed longer emission and low quantum yield in polar solvent. Taken together, the inventors demonstrated that by two-step red-shift modification of curcumin, the inventors were able to push its emission wavelength into ideal emission range for NIR probes. Additionally, these modifications produced a large stokes shift and improved quantum yield of CRANAD-2. The synthesized compound produced the longest emission and the largest stokes shift among the existing probes for senile plaque detection {3}.

In Vitro Testing.

Binding Properties with Aβ Aggregates In Vitro.

Figure 6:
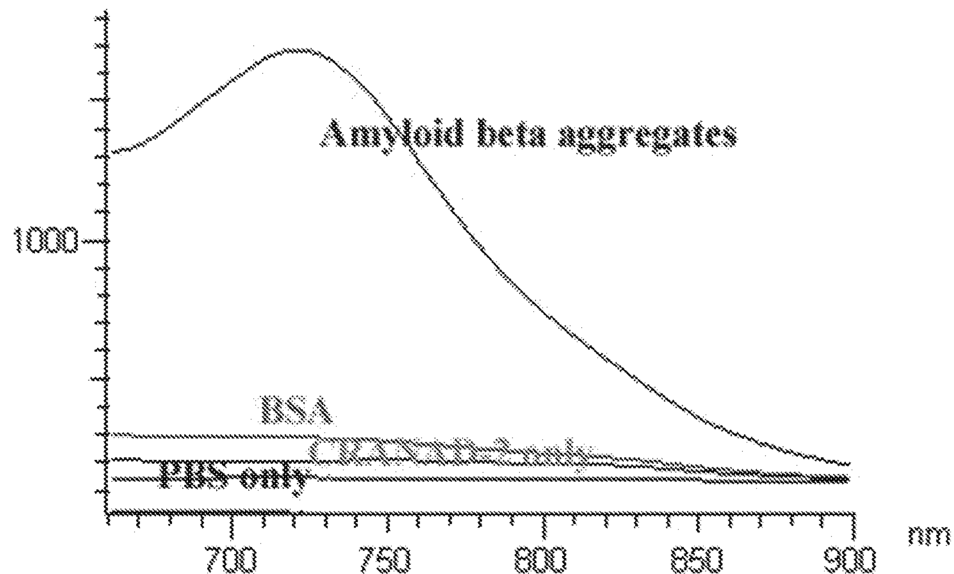
FIG. 6. The Fluorescent intensity comparison of CRANAD-2 with Aβ40 aggregates (20 μg/ml), BSA (20 μg/ml), CRANAD-2 only (5.0 μM).

First, the inventors tested the binding ability of CRANAD-2 towards artificial Aβ aggregates, which could be generated from Aβ40 peptide by incubation with metal ions such as $Cu^{2+}$ and $Zn^{2+}$ or by long time stirring, and could be then confirmed by TEM {43}. We compared the fluorescence intensity of CRANAD-2 with PBS (pH 7.4), Aβ40 peptide, and Aβ40 aggregates generated from $Cu^{2+}$ induced aggregation. While we did not observe any significant difference between PBS and Aβ40 peptide monomer, there was a remarkable 70 fold intensity increase in the presence of Aβ40 aggregates (FIG. 6). This result suggested that our probe could be "turned on" upon interacting with its substrate, and this was reflected by the changes in quantum yield from 0.006 in PBS to 0.40 after binding to Aβ40 aggregates. A significant blue-shift (100 nm) was observed as well after binding with Aβ40 aggregates, indicating the insertion of the dye into hydrophobic environment of the aggregates. Moreover, CRANAD-2 displayed a remarkable lifetime change after it bound to the aggregates (FIG. 4). The $\tau_1$ of probe alone was 0.3 s, while its $\tau_1$ changed to 0.7 s upon its binding to the aggregates. Taken together, the "turn on" phenomenon, quantum yield increase, and significant blue-shift point to "smart" nature of CRANAD-2 towards Aβ40 aggregates. These characteristics are believed to be essential requirements for utilizing this probe for in vivo imaging.

Figure 5:
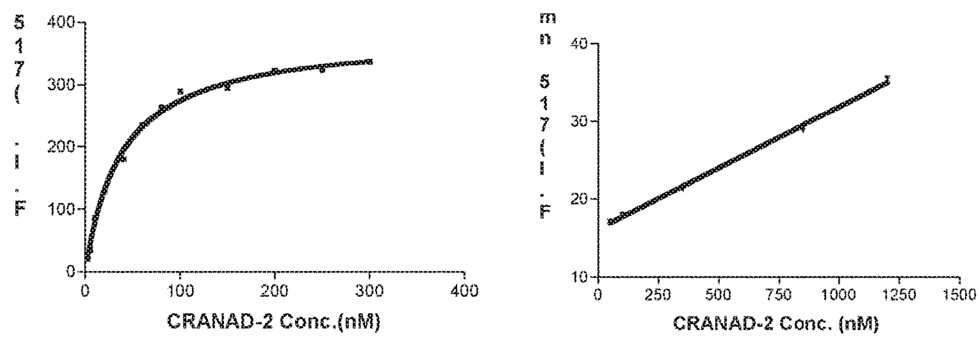
FIG. 5. Binding constant measurement of CRANAD-2 with Aβ aggregates (left), and the right linear graph ($R^2$=0.9944) indicates that CRANAD-2 isn't self-quenched with the range tested.

Binding constant (Kd) of CRANAD-2 towards Aβ aggregates was measured by fluorescence intensity (F.I.) with various concentrations of the prob. By fitting the data to nonlinear one-binding site regression model, the calculated binding constant was Kd=38.69±2.77 nM ($R^2$=0.9952, FIG. 5 left). Linear concentration dependence of the probe in PBS buffer indicated the absence of self-quenching within the range tested (FIG. 5, right) This binding constant was significantly higher than that of Thioflavin T (Kd=580 nM) {44} and than that of AOI 987 (Kd=220±130 nM) {24} and was close to that of NIAD-4 (Kd=10.0 nM) {7}.

Additionally, the inventors also examined the binding property of CRANAD-1. Although the Kd=1.0 nM was higher than that of CRANAD-2, there was no obvious fluorescence increasing after it bound to the artificial aggregates (data not shown). Therefore, CRANAD-1 can not be considered as a "smart" probe for Aβ aggregates.

BSA Binding and Stability of the Probe.

Since serum albumin is the most abundant plasma protein, it was important to test whether the probe had any affinity toward this protein. To test this the inventors incubated CRANAD-2 probe with BSA. For controls, the inventors used PBS buffer alone, the probe incubated in PBS alone, and with Aβ40 aggregates. The inventors did not observe any significant change in fluorescence when the probe was incubated with BSA, PBS, whereas there was a significant peak of fluorescence change after incubation with Aβ 40 aggregates (FIG. 6). In addition, the inventors tested CRANAD-2 stability by incubating the probe ($4\times10^{-6}$M) with human serum for 2 hours at 37° C. After ethyl acetate extraction, both fluorescence and HPLC spectra showed about 70% recovery of the probe indicating its relative stability.

Lipophilicity Testing.

In order for the probe to cross blood brain barrier, its lipophilicity (log P) should be within 2-5 range. Testing the log P value for CRANAD-1 by a standard octanol/water method produced log P=3.0, while the same value for CRANAD-1 was found to be log P=1.7. These results indicate that CRANAD-2 holds promise as a BBB penetrating probe. Furthermore, it displays significantly higher log P value than that of the parent compound curcumin {35}.

Histological Studies.

Figure 7:
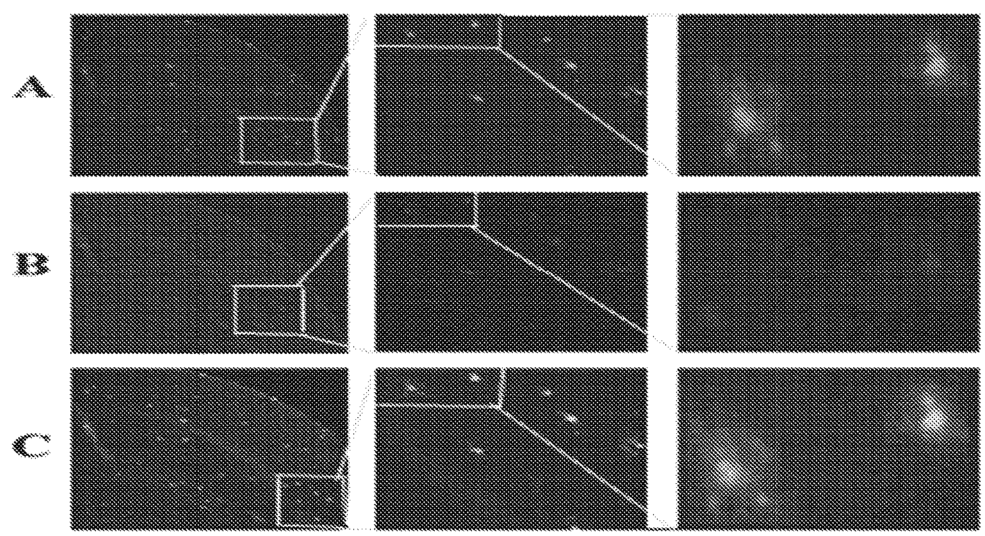
FIG. 7. Histological staining with CRANAD-2 (0.01% in acetone-ethanol-water (20:30:50). a,b Cortex stained by CRANAD-2; c, co-staining with Thioflavin S, left, CRANAD-2 (red colored) and right as merged with thioflavin S staining.

To demonstrate that CRANAD-1 was capable of detecting Aβ plaques, the inventors incubated sliced brain tissue from Tg2576 mice with the probe. The inventors observed a bright signal coming from the tissue, which co-localized with the signal from Thioflavin S stained sections (FIG. 7). These results confirmed CRANAD-2 specificity towards Aβ plaques.

In Vivo Testing and Imaging.

BBB Penetrating Testing.

Figure 8:
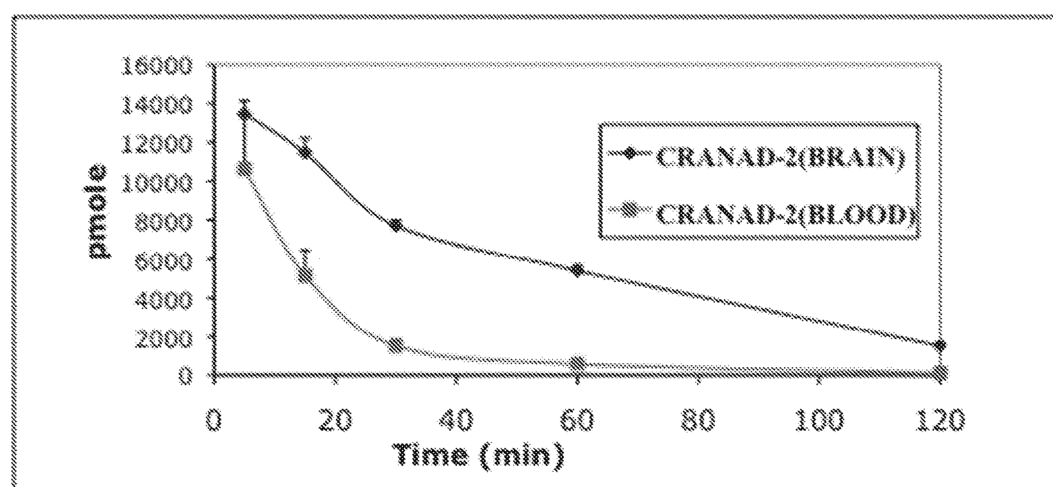
FIG. 8. The clearance curve of CRANAD-2 in blood (lower curve) and brain (upper curve) in Balb/C mice (n=3) at various time points after i.v injection of 10 mg/kg of the probe.

To demonstrate that the CRANAD-2 probe of the present invention possessed BBB penetrating ability, the inventors intravenously injected wild type mice with CRANAD-2 and scarified them at different time points followed by perfusion. In addition, to follow the probe clearance the inventors drew blood samples at each time point. Both fluorescence spectrum and HPLC analysis of the brain homogenate demonstrated the presence of CRANAD-2 in the tissue confirming its capability to cross BBB. LC-MS results also confirmed that the major component of the ethyl acetate extraction was CRANAD-2. The probe demonstrated a rapid clearance from blood while the clearance from the brain was significantly slower (FIG. 8).

In Vivo Imaging.

Figure 11:
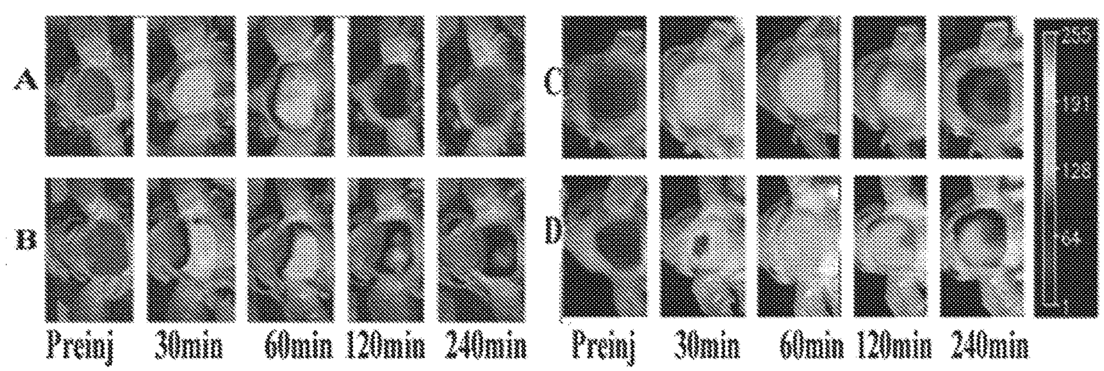
FIG. 11. Representative images of Tg2576 and littermate at different time points before and after i.v. injection of 5.0 mg/kg CRANAD-2. (A) 11-month old littermate; (B) 11-month old Tg2576 (mice of A and B showed similar background fluorescence signal); (C) 19-month old control mouse; (D) 19-month old Tg2576 (mice of C and D showed similar background fluorescence signal).

Transgenic 11-month and 19-month old Tg2576 mice were used to validate the feasibility of CRANAD-2 as NIR imaging probe. Aged-matched wild type littermates served as controls. Images were recorded before and after i.v. injection of CRANAD-2 at 5.0 mg/Kg dosage. For mice with comparable background fluorescence ($F_{pre}$) (FIGS. 11A vs B, and C vs D), the declining of fluorescence signals was considerably slower for both 11- and 19-month old Tg2576 than that for the control groups (FIGS. 11A vs B, and C vs D). Overall, the fluorescence intensity of both transgenic groups was higher than that of the control groups at 30 min, 60 min, 120 min, and 240 min after injection. Furthermore, the signals from 19-month old Tg2576 (FIG. 11D) were remarkably brighter at all time points. However, from the reported images of AOI 987, no difference was seen at 30 min. or 60 min. This result was not unexpected, since AOI 987 could not be considered a "smart" probe, On the contrary, for the mice with similar background signals, the inventors results not only showed a difference at 120 min and 240 min, but also at 30 min. and 60 min. for both 11- and 19-month old mice. This result this was due to the "smart" nature of CRANAD-2 probe in vivo.

Figure 9:
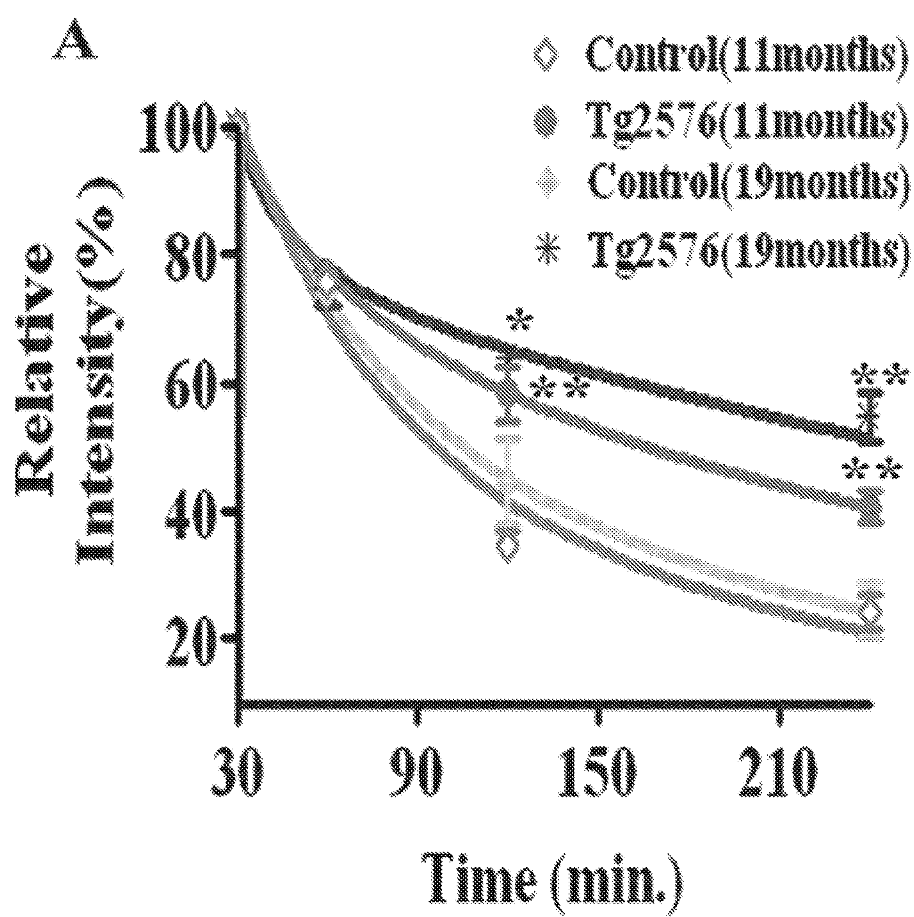
FIG. 9. (A) Relative fluorescence signal decay curves for 11- and 19 month-old transgenic Tg2576 and their littermates after i.v injection of 5.0 mg/kg CRANAD-2 probe. The curves were obtained by fitting with non-linear regression, two binding sites model (Prism 3.0); (B-C) the incremental folds of fluorescence signal after normalizing to background signal; (B) 11-month old mice, and (C) 19-month old mice. *: p=<0.05, **: p=<0.01.
Figure 9:
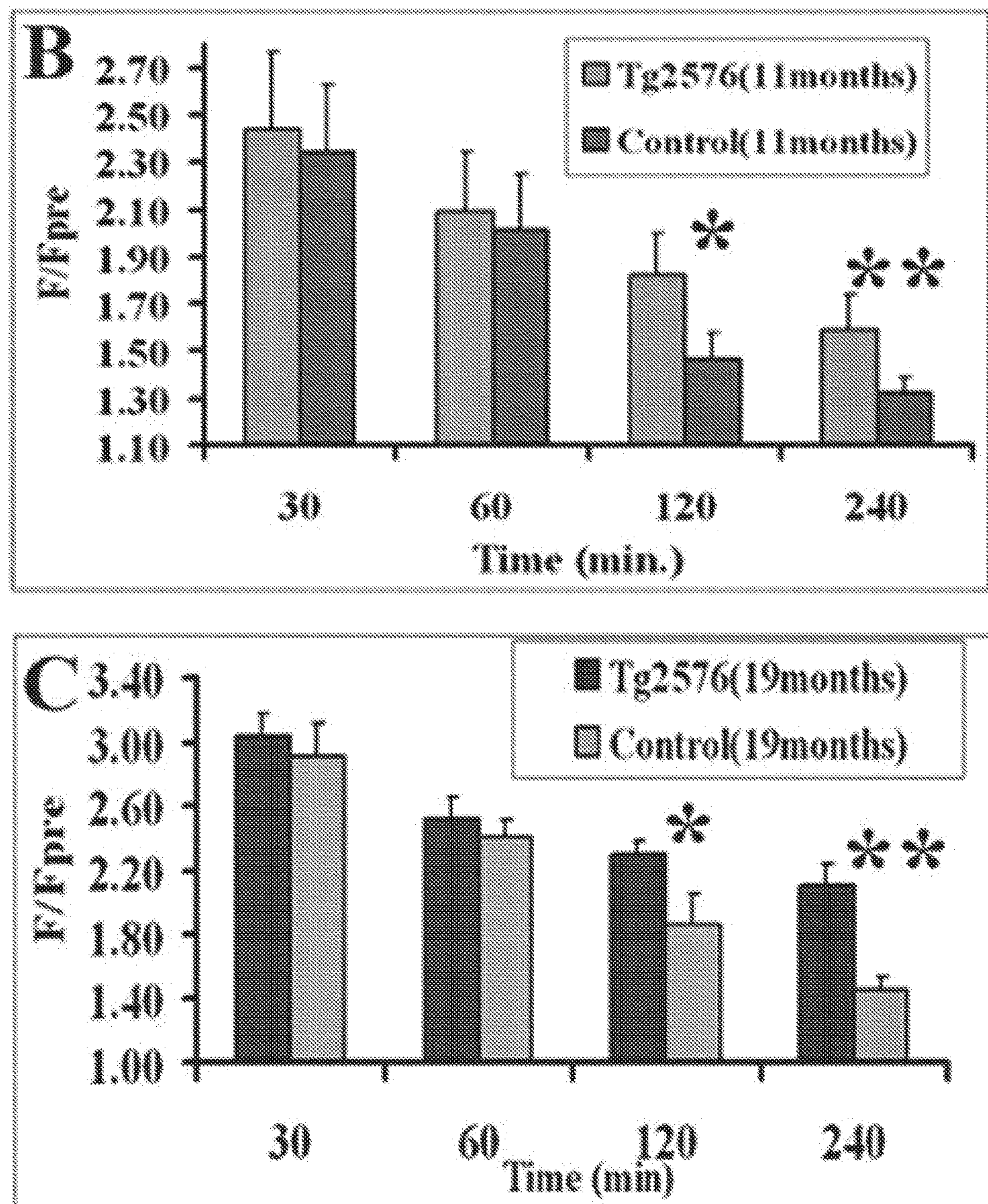

Semi-quantitative analysis of these images was conducted with selected region of interested (ROI), and two sets of data were generated. By normalizing the fluorescence intensity to that of 30 min. after the injection of the probe, we were able to create four well-fit decay curves with non-linear regression for two binding site model (Prism 3.0) for both 11- and 19-months old groups ($R_2$=0.96, 0.97, 0.97, and 0.94 for 11-month control, tg2576, and 19-month control and tg2576 respectively) (FIG. 9A). By normalizing the signal to background fluorescence intensity ($F_{pre}$), and using the ratio between fluorescence intensity at time points studied (($F_{(t)}$) and $F_{pre}$) we could compare the signal change in Tg2576 group to that of the control group (FIGS. 9B,C)(e.g. $F_{(t)}/F_{pre}$). Details of these methods are described in Materials and Methods contained herein.

As expected, relative fluorescence decays ($I_{rel(t)}$) (FIG. 9A) of transgenic group were remarkably slower than that of the wild type group (equation (1) for $I_{rel(t)}$ was described in the Material and Methods section). 11-Month old Tg2576 group displayed significant differences in decay rates at 120 min. and 240 min over the control group (23% at 120 min. P=0.004, and 16% at 240 min, P=0.006). This result was similar to the values reported by Gremlich group (16), where 10-20% difference between the two groups was shown at different time points when 10-month old mice were used. For 19-month old group, significant differences were observed at 120 min and 240 min. as well (20% at 120 min., P=0.02, and 30% at 240 min., P=0.003), and the largest difference was seen at 240 min after probe administration. As predicted, there was no significant difference between 11- and 19-months old control mice at all time points. On the contrary, the inventors observed that 19-month Tg2576 group exhibited 11% and 13% slower decay rates compared to that of 11-month old Tg2576 mice at 120 min. and 240 min. respectively (P=0.1 at 120 min, and P=0.02 at 240 min.).

By normalizing the background fluorescence signal, the inventors found that the signal incremental fold ($F_{(t)}/F_{pre}$)) in Tg2576 group were higher than that in the control groups at all time points (FIGS. 9B, C). This result, however, is not surprising, considering that CRANAD-2 probably exhibits its "lighting-up" ability by its "turn-on" property upon binding to the Aβ fibrils and plaques. Given that the ratio of the probe accumulation in Aβ fibrils and plaques over the total probe remained increased after injection, the inventors anticipated that the $F_{(t)}/F_{pre}$ gap between Tg2576 group and the controls would increase with longer time. Indeed, significantly larger differences in $F_{(t)}/F_{pre}$ values were obtained at 120 min. and 240 min. for both 11- and 19-month mice (0.52, P=0.03; 0.45, P=0.01; for 11-month old at 120 min., 240 min., and 0.43, P=0.05; 0.65, P=0.005 for 19-month old at 120 min., 240 min.). Since relative fluorescence decay ($I_{rel(t)}$) reflects the relative concentration of the probe remained at the studied time points, and $F_{(t)}/F_{pre}$ stands for the incremental fold of fluorescence signal the inventors concluded that the "smart" amplification factor (SAF) in vivo probably could be calculated as the ratio of the difference between ($F_{(t)}/F_{pre}$) and $I_{rel(t)}$ in transgenic and control groups (see detailed descriptions for this calculation in Material and Method section, equation (2)). If the ratio>1.0, the probe is "smart" in vivo. According to this calculation, CRANAD-2 is a "smart" probe in vivo at 120 min and 240 min for both 11- and 19-months groups.

Histological Correlation

Figure 10:
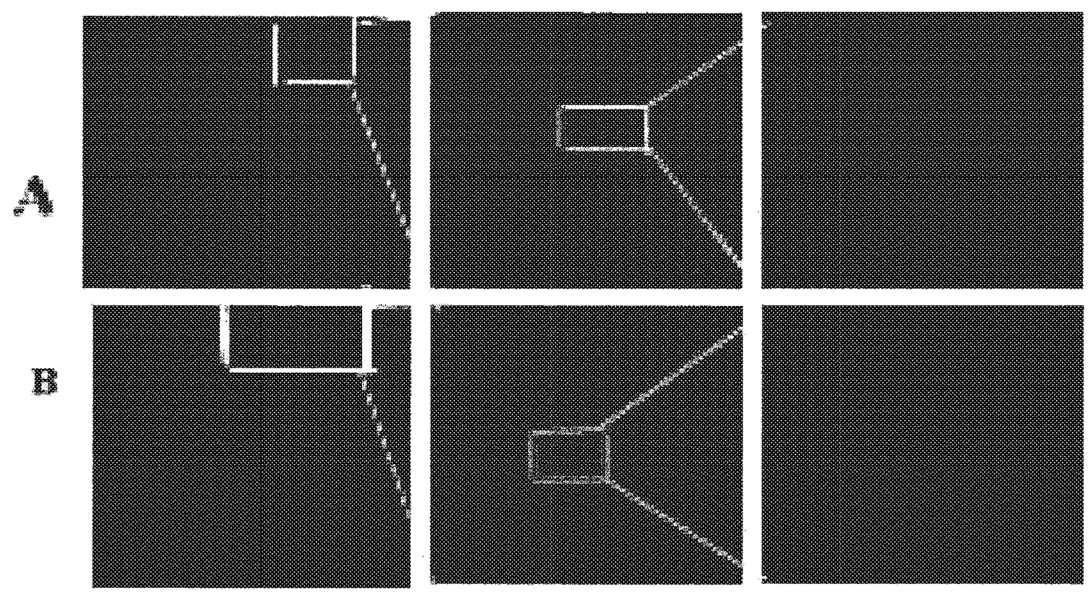
FIG. 10. Ex vivo histology of 19 month-old mice sacrificed at 4 h. after i.v. injection of 10 mg/kg of CRANAD-2. (A) cortex of control mice, left: 2×; middle: 10×, the region highlighted in left panel; right: 40×, the region highlighted in middle panel; (B) cortex of Tg2576 mice.

To obtain ex vivo confirmation of the probe binding, mice at different ages were i.v injected with 10 mg/kg of CRANAD-2 probe, perfused and scarified at 1 h after injection. The inventors could not find obvious senile plaques in 11-month old transgenic and wild-type mice after injection of CRANAD-1 probe and thioflavin S staining. However, senile plaques were observed in 19-month old transgenic mice after injection of the probe CRANAD-2 (FIG. 10). These results further confirm that CRANAD-1 probe can penetrate BBB and label senile plaques in vivo.

Discussion.

The present invention provides a NIR Aβ plaque-specific fluorescent probe CRANAD-2. This probe is the first example of difluoroborate diketone, used as an NIR fluorescent dye for cell, tissue, and in vivo imaging.

Surprisingly, the probe of the present invention meets the requirements for a particularly useful NIR probe for detecting Aβ aggregates. First, the probe has a molecular weight is only 400 dalton. Its log P is 3.0, which is within the range for the recommended lipophilicity (log p 2-5) for CNS drugs that have high potential to penetrate brain blood barrier. Second, utilizing a two-step red-pushing strategy, the inventors obtained the compound with fluorescence emission that falls into the ideal "optical window" (650-900 nm) for NIR imaging.

At the same time CRANAD-2 probe also exhibits a large stoke shift (140 nm for PBS only, and 70 nm for PBS with Aβ aggregates). Noteworthy, the reported AOI 987 probe had a stokes shift of only 20 nm. Moreover, CRANAD-2 probe showed high quantum yield upon binding to aggregates (40%) though its quantum yield was low (0.6%) in PBS buffer.

Third, the probe exhibited considerable stability in serum in vitro which was further confirmed in our in vivo studies. Additionally, it did not show any significant binding to BSA, the major serum protein component. Fourth, the probe possesses high affinity to Aβ aggregates, with the $K_d$ comparable to Thioflavin T and NIAD-4, and being significantly higher than AOI 987. Fifth, CRANAD-2 displayed specific staining with Aβ plaques from aged transgenic mice brain tissue, indicating that the probe has particular selectivity for Aβ plaques over other components of brain tissue.

Sixth, this probe displayed specific properties of a "smart" probe since its emission wavelength and fluorescence intensity and lifetime were highly sensitive to the binding with Aβ plaques. After binding to Aβ plaques, the probe was "turned on" and displayed a 70-fold increase in fluorescence intensity and 60 nm blue-shift, and remarkable lifetime change upon binding to the aggregates.

Finally, the inventors demonstrated that this probe could be used for early AD detection in the animal model. It has been shown that Tg2576 mice 11-13 months of age show a 14-fold increase in Aβ (1-42/43) over those at 2-8 months of age, and the 9-13 months is believed as initiate stage for senile plaque formation {45}.

As reported by Gremlich, there is no significant dissimilarity at 6-month old of transgenic and littermates both in behavior tests and histological staining, and the difference could be detected around 9-month old. They found that the difference at 10-month is about 10-20% between transgenic and wild type littermates, and the inventor's outcomes of 11-month is comparable to their results. Although the inventors and others {24} didn't observe obvious plaques in 10 or 11 month-old Tg2576 mice by ex vivo examine, it is possible that these mice already have considerable concentration of fibrils or aggregates, which couldn't be seen with histological staining, but it could, as in vitro experiments indicated, interact with the inventors' probe and generate the "turn on" fluorescence signal. However, for 19-month old mice, the inventors not only proved by ex vivo histology that our probe could specifically bind to senile plaques, but also demonstrated that the progress of Aβ plaques generation could be monitored by using our NIR probe. Additionally, by comparing mice with similar background fluorescence, the "smart" nature of our probe could be observed in vivo. The inventor's results points to the feasibility of early detection and progress monitoring of AD pathology with the inventors' NIR imaging probe CRANAD-2.

The design of the inventors' probe was based on curcumin, which had been reported as a specific histological probe, as well as a probe for in vivo two-photon microscopy of senile plaques. The inventors' modifications not only kept its specificity to Aβ deposits, but also introduced a new "smart" property, which curcumin itself did not possess. It is not clear whether the binding mechanism of curcumin and the inventors' probe are the same; however, no particular mode of operation is adopted herein. However, the blue-shift and fluorescence intensity increase upon binding to aggregates indicated the association of the molecule with hydrophobic environment, which could be represented by the segment LVKFFA considered to be the most hydrophobic part of Aβ40 and Aβ42 peptides.

The probe of the present invention has a potential not only for diagnosis, but also for a possible treatment for AD. Additionally, the inventors' probe may have better effect because of its beneficial log P value.

Although Bodipy dyes, a class of dyes with difluoro-N, N-boryl ring, have been well documented {38; 39; 40}, the corresponding compounds with difluoro-dioxaboryl ring have been less studied. The inventors believe that the difluoro-dioxaboryl dyes could be developed as imaging probes for other pathologies, and serve as an alternative for the most popular NIR Cy5.5 dye, which limitations include narrow stokes shift. Additionally, the inventors' two-step red-shift pushing strategy applied here could be used for modification of other dyes to improve their capacity as imaging probes. In particular, the inventors' results indicate that the formation of 2,2-difluoro-1,3-dioxaboryl ring was advantageous for red-shift pushing. In short, the approach disclosed herein provides an opportunity for the design and application of a new category of fluorescence imaging probes.

Example 2

AD Tissue Staining

Figure 12:
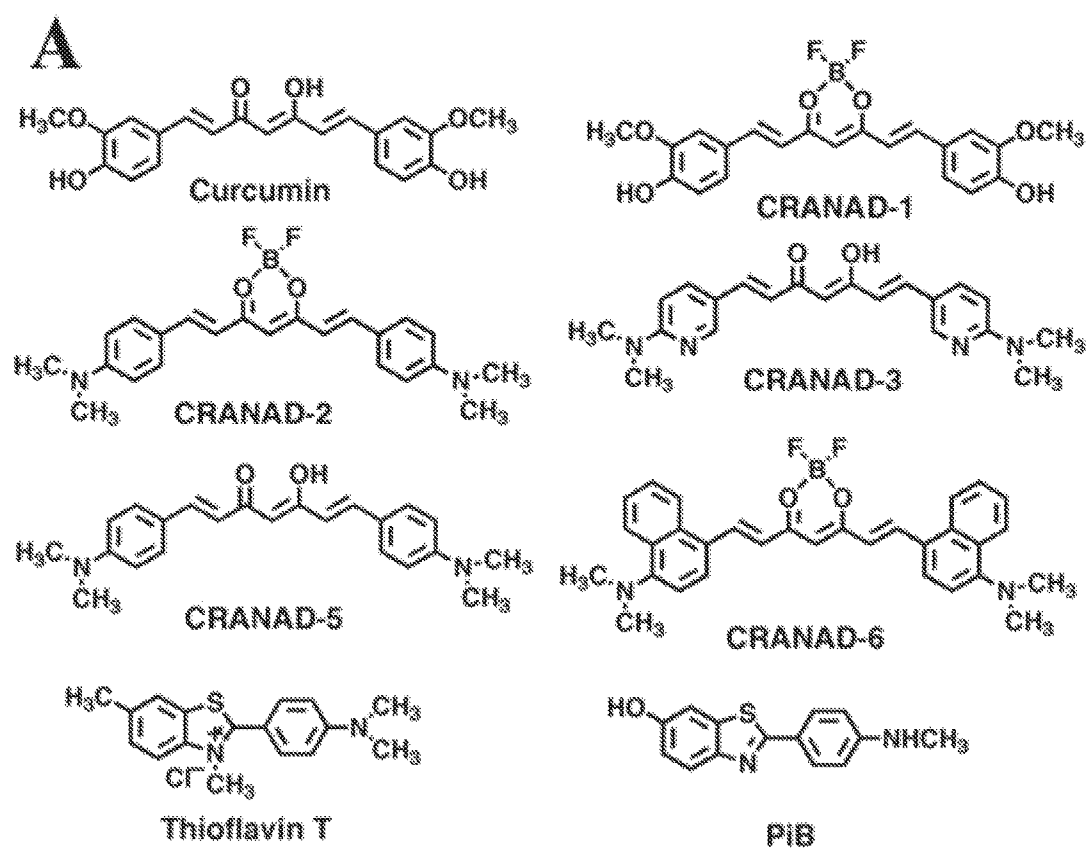
FIG. 12. (A) the chemical structures of compounds tested; (B) histology of CRANAD-3 and CRANAD-5 with APP-PS1 brain section, left: CRANAD-3 or CRANAD-5 staining; middle: thioflavin T; right: merge (40×); (C) fluorescence spectrum of CRANAD-3, 5 and thioT in absence of and in presence of Aβ40 aggregates.
Figure 12:
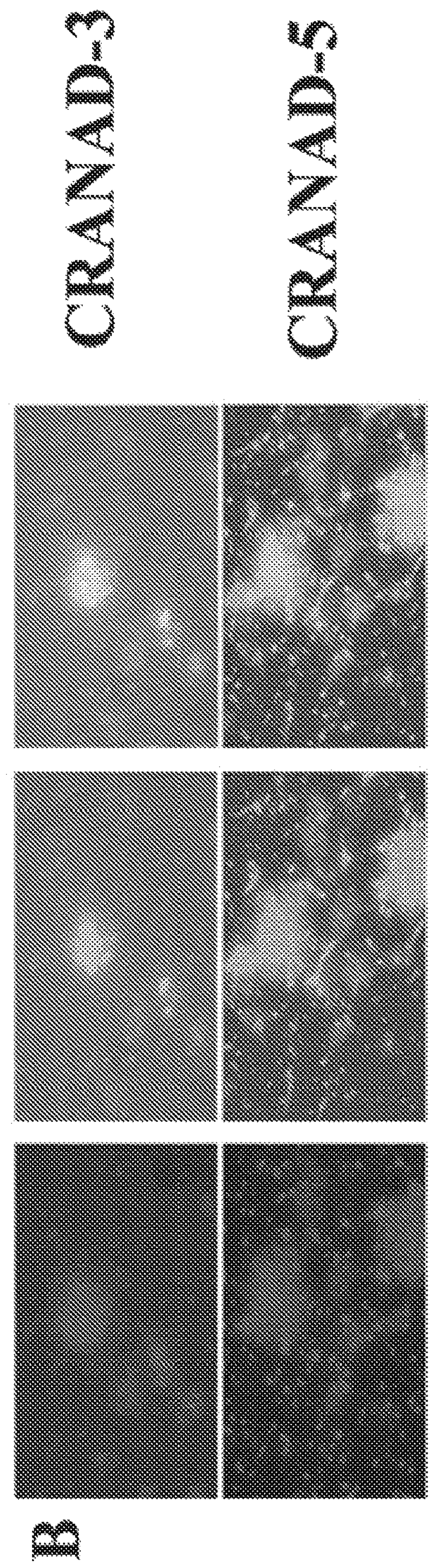
Figure 12:
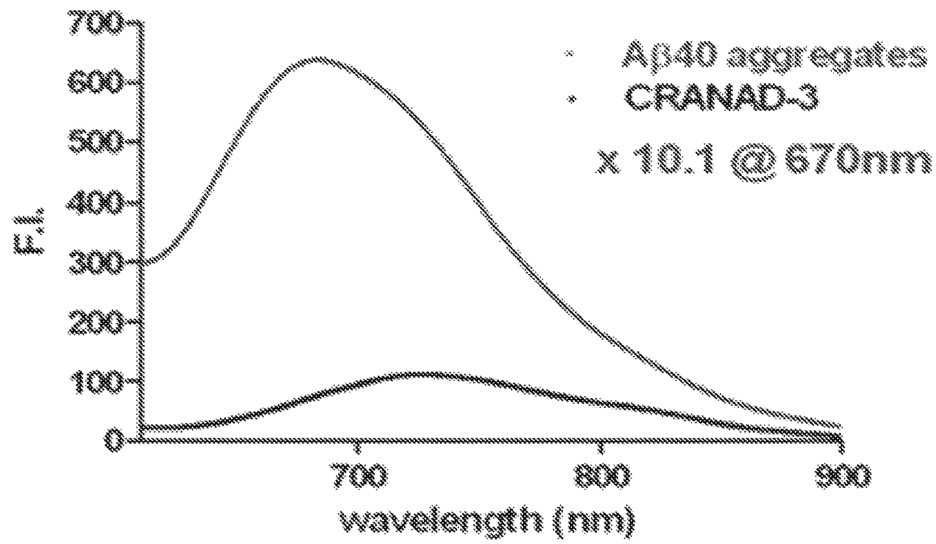
Figure 12:
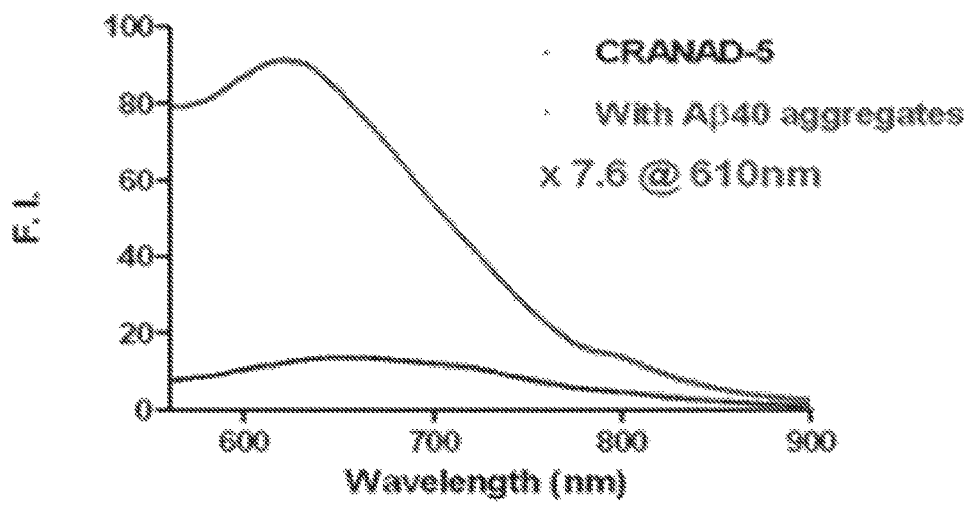

The inventors conducted tissue staining with 25 micron brain sections from 12-month old APP-PS1 mice by all the compounds listed in FIG. 12. As reported, curcumin, PiB, thioflavin T and CRANAD2 stained the plaques brightly; while as expected, CRANAD-2, CRANAD-3 and CRANAD-5 yielded good staining as well (FIG. 12B). These data indicate that these compounds are specific to Aβ plaques.

Preparation of CRANAD-3 and CRANAD-5 Compounds

Boric oxide (700.0 mg, 10.0 mmol) was dissolved in DMF (10.0 mL) at 120° C. Ensuring most of boric oxide dissolved was very crucial for high yield. To this solution, acetylacetone (1.1 mL, 10.0 mmol) was added, followed by tributyl borate (5.4 mL, 20.0 mmol) at 110° C. and stirred for 5 min. To the above borate complex, 4-N,N'-dimethylamino-benzaldehyde (3.1 g, 20.0 mmol) was added and stirred for 5 min. A mixture of 1,2,3,4-tetrahydroquinoline (0.2 mL) and acetic acid (0.4 mL) in DMF (4.0 mL) was added to the reaction mixture and heated to 110° C. for 2 h. After cooling to room temperature, the reaction mixture was poured into ice-water (500 mL), and the reddish precipitate was collected, which was further purified by silica gel column using ethyl acetate/hexanes (50:50) as eluent to give CRANAD-5 (1.8 g). $^{1}$H NMR (DMSO-d6) δ; $^{13}$C NMR (DMSO-d6) δ(ppm). The spectra were consistent with the reported value. CRANAD-3 was synthesized by following the similar procedure for CRANAD-5, or by the similar procedure for CRANAD-2 described in a previous example.

Aβ Aggregates Detection in Solution by Fluorescence Spectrum

Figure 12C:
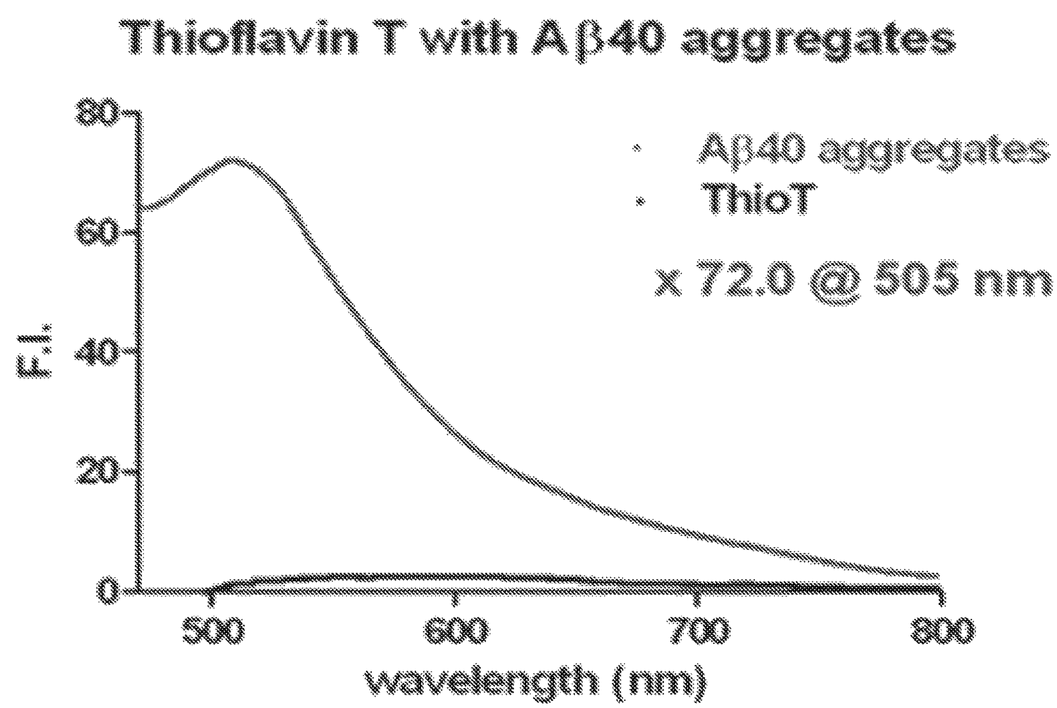

The inventors generated Aβ40 aggregates by stirring the solution at room temperature for 3 days, and TEM confirmed the existence of aggregates. They then incubated 250 nM of the compounds with 250 nM of Aβ40 aggregates (calculation based on monomer) in PBS for one minute, and then measured the fluorescence spectra of the solutions. The results showed that CRANAD1, and CRANAD6 were not "smart" fluorescence probes; while CRANAD-2, 3, 5, curcumin and thioflavin T displayed intensity increases, and CRANAD-2, 3, 5 and curcumin had wavelength blue-shifts as well (FIG. 12C). Thioflavin T, the standard compound used for assessing the degree of fibrillating, was reported as a "smart" optical probe, and the results were consistent with this claim. Thioflavin T yielded the highest FI amplification (72-fold), and CRANAD-3 showed the highest FI reading (FIG. 12C). In addition, it was interesting to note that PiB displayed a red-shift and slightly FI decrease. This example illustrates the utility of compounds CRANAD-2, CRANAD-3 and CRANAD-5 as probes for the detection of Aβ plaques.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

REFERENCES

1. Selkoe, D. J., *Translating cell biology into therapeutic advances in Alzheimer's disease*. Nature, 1999. 399(6738 Suppl): p. A23-31.
2. Stokin, G. B., et al., *Axonopathy and transport deficits early in the pathogenesis of Alzheimer's disease*. Science, 2005. 307(5713): p. 1282-8.

3. Tanzi, R. E., R. D. Moir, and S. L. Wagner, *Clearance of Alzheimer's Abeta peptide: the many roads to perdition*. Neuron, 2004. 43(5): p. 605-8.

4. Bacskai, B. J., et al., *Imaging of amyloid-beta deposits in brains of living mice permits direct observation of clearance of plaques with immunotherapy*. Nat Med, 2001. 7(3): p. 369-72.

5. Lee, V. M., *Abeta immunization: moving Abeta peptide from brain to blood*. Proc Natl Acad Sci USA, 2001. 98(16): p. 8931-2.

6. Raymond, S. B., et al., *Smart optical probes for near-infrared fluorescence imaging of Alzheimer's disease pathology*. Eur J Nucl Med Mol Imaging, 2008.

7. DeMattos, R. B., et al., *Peripheral anti-A beta antibody alters CNS and plasma A beta clearance and decreases brain A beta burden in a mouse model of Alzheimer's disease*. Proc Natl Acad Sci USA, 2001. 98(15): p. 8850-5.

8. Meyer-Luehmann, M., et al., *Rapid appearance and local toxicity of amyloid-beta plaques in a mouse model of Alzheimer's disease*. Nature, 2008. 451(7179): p. 720-4.

9. Gong, C. X., et al., *Post-translational modifications of tau protein in Alzheimer's disease*. J Neural Transm, 2005. 112(6): p. 813-38.

10. Iqbal, K., et al., *Tau pathology in Alzheimer disease and other tauopathies*. Biochim Biophys Acta, 2005. 1739(2-3): p. 198-210.

11. Santacruz, K., et al., *Tau suppression in a neurodegenerative mouse model improves memory function*. Science, 2005. 309(5733): p. 476-81.

12. Roberson, E. D., et al., *Reducing endogenous tau ameliorates amyloid beta-induced deficits in an Alzheimer's disease mouse model*. Science, 2007. 316(5825): p. 750-4.

13. Ramsden, M., et al., *Age-dependent neurofibrillary tangle formation, neuron loss, and memory impairment in a mouse model of human tauopathy (P301L)*. J Neurosci, 2005. 25(46): p. 10637-47.

14. Dubois, B., et al., *Research criteria for the diagnosis of Alzheimer's disease: revising the NINCDS-ADRDA criteria*. Lancet Neurol, 2007. 6(8): p. 734-46.

15. Mathis, C. A., Y. Wang, and W. E. Klunk, *Imaging beta-amyloid plaques and neurofibrillary tangles in the aging human brain*. Curr Pharm Des, 2004. 10(13): p. 1469-92.

16. Hintersteiner, M., et al., *In vivo detection of amyloid-beta deposits by near-infrared imaging using an oxazine-derivative probe*. Nat Biotechnol, 2005. 23(5): p. 577-83.

17. Skovronsky, D. M., et al., *In vivo detection of amyloid plaques in a mouse model of Alzheimer's disease*. Proc Natl Acad Sci USA, 2000. 97(13): p. 7609-14.

18. Nesterov, E. E., et al., *In vivo optical imaging of amyloid aggregates in brain: design of fluorescent markers*. Angew Chem Int Ed Engl, 2005. 44(34): p. 5452-6.

19. Higuchi, M., et al., *19F and 1H MRI detection of amyloid beta plaques in vivo*. Nat Neurosci, 2005. 8(4): p. 527-33.

20. Poduslo, J. F., et al., *Design and chemical synthesis of a magnetic resonance contrast agent with enhanced in vitro binding, high blood-brain barrier permeability, and in vivo targeting to Alzheimer's disease amyloid plaques*. Biochemistry, 2004. 43(20): p. 6064-75.

21. Jack, C. R., Jr., et al., *In vivo visualization of Alzheimer's amyloid plaques by magnetic resonance imaging in transgenic mice without a contrast agent*. Magn Reson Med, 2004. 52(6): p. 1263-71.

22. Lee, S. P., et al., *Visualization of beta-amyloid plaques in a transgenic mouse model of Alzheimer's disease using MR microscopy without contrast reagents*. Magn Reson Med, 2004. 52(3): p. 538-44.

23. Helpern, J. A., et al., *Quantitative MRI assessment of Alzheimer's disease*. J Mol Neurosci, 2004. 24(1): p. 45-8.

24. Helpern, J. A., et al., *MRI assessment of neuropathology in a transgenic mouse model of Alzheimer's disease*. Magn Reson Med, 2004. 51(4): p. 794-8.

25. Wadghiri, Y. Z., et al., *Detection of Alzheimer's amyloid in transgenic mice using magnetic resonance microimaging*. Magn Reson Med, 2003. 50(2): p. 293-302.

26. Garcia-Alloza, M., et al., *Curcumin labels amyloid pathology in vivo, disrupts existing plaques, and partially restores distorted neurites in an Alzheimer mouse model*. J Neurochem, 2007. 102(4): p. 1095-104.

27. Bacskai, B. J., et al., *Molecular imaging with Pittsburgh Compound B confirmed at autopsy: a case report*. Arch Neurol, 2007. 64(3): p. 431-4.

28. D'Amore, J. D., et al., *In vivo multiphoton imaging of a transgenic mouse model of Alzheimer disease reveals marked thioflavine-5-associated alterations in neurite trajectories*. J Neuropathol Exp Neurol, 2003. 62(2): p. 137-45.

29. Li, Q., et al., *Solid-phase synthesis of styryl dyes and their application as amyloid sensors*. Angew Chem Int Ed Engl, 2004. 43(46): p. 6331-5.

30. Shishodia, S., G. Sethi, and B. B. Aggarwal, *Curcumin: getting back to the roots*. Ann N Y Acad Sci, 2005. 1056: p. 206-17.

31. Siwak, D. R., et al., *Curcumin-induced antiproliferative and proapoptotic effects in melanoma cells are associated with suppression of IkappaB kinase and nuclear factor kappaB activity and are independent of the B-Raf/mitogen-activated/extracellular signal-regulated protein kinase pathway and the Akt pathway*. Cancer, 2005. 104(4): p. 879-90.

32. Aggarwal, B. B., et al., *Curcumin suppresses the paclitaxel-induced nuclear factor-kappaB pathway in breast cancer cells and inhibits lung metastasis of human breast cancer in nude mice*. Clin Cancer Res, 2005. 11(20): p. 7490-8.

33. Aggarwal, S., et al., *Curcumin (diferuloylmethane) down-regulates expression of cell proliferation and anti-apoptotic and metastatic gene products through suppression of IkappaBalpha kinase and Akt activation*. Mol Pharmacol, 2006. 69(1): p. 195-206.

34. Yang, F., et al., *Curcumin inhibits formation of amyloid beta oligomers and fibrils, binds plaques, and reduces amyloid in vivo*. J Biol Chem, 2005. 280(7): p. 5892-901.

35. Ryu, E. K., et al., *Curcumin and dehydrozingerone derivatives: synthesis, radiolabeling, and evaluation for beta-amyloid plaque imaging*. J Med Chem, 2006. 49(20): p. 6111-9.

36. Roth, H. J. and B. Miller, [*on the Color Reaction between Boric Acid and Curcumin. I. Boric Acid-Curcumin Complexes*]. Arch Pharm (Weinheim), 1964. 297: p. 617-23.

37. Roth, H. J. and B. Miller, [*On the color reaction between boric acid and curcumin. II. On the constitution of rosocyanins and rubrocurcumins*]. Arch Pharm Ber Dtsch Pharm Ges, 1964. 297(11): p. 660-73.

38. Ulrich, G., R. Ziessel, and A. Harriman, *The chemistry of fluorescent bodipy dyes: versatility unsurpassed*. Angew Chem Int Ed Engl, 2008. 47(7): p. 1184-201.

39. Zhang, G., et al., *Multi-emissive difluoroboron dibenzoylmethane polylactide exhibiting intense fluorescence and*

*oxygen-sensitive room-temperature phosphorescence*. J Am Chem Soc, 2007. 129(29): p. 8942-3.

40. Hales, J. M., et al., *Bisdioxaborine polymethines with large third-order nonlinearities for all-optical signal processing*. J Am Chem Soc, 2006. 128(35): p. 11362-3.

41. Mason, W., *Fluorescent and Luminescent Probes for Biological Activity*. Second Edition ed. 1999: Academic Press.

42. Zhao, H., et al., *Coumarin-based inhibitors of HIV integrase*. J Med Chem, 1997. 40(2): p. 242-9.

43. Weber, W. M., et al., *Anti-oxidant activities of curcumin and related enones*. Bioorg Med Chem, 2005. 13(11): p. 3811-20.

44. Jun, S. and S. Saxena, *The aggregated state of amyloid-beta peptide in vitro depends on Cu2+ ion concentration*. Angew Chem Int Ed Engl, 2007. 46(21): p. 3959-61.

45. Klunk, W. E., et al., *Uncharged thioflavin-T derivatives bind to amyloid-beta protein with high affinity and readily enter the brain*. Life Sci, 2001. 69(13): p. 1471-84.

46. Hsiao, K., et al., *Correlative memory deficits, Abeta elevation, and amyloid plaques in transgenic mice*. Science, 1996. 274(5284): p. 99-102.

What is claimed is:

1. A method for detecting an amyloid beta plaque in a sample, comprising:

(a) contacting a sample comprising an amyloid beta plaque with a compound, such that said compound binds the amyloid beta plaque, wherein the compound has the formula $Ar^1$-L-$Ar^2$ and wherein: L is a divalent linking group comprising an alkenylene having 5 to 15 backbone carbon atoms, wherein at least two of the backbone carbon atoms form part of a difluoroboronate ring; and $Ar^1$ and $Ar^2$ are each independently alkyl amine-substituted aryl or heteroaryl groups;

(b) illuminating said compound bound to the amyloid beta plaque with near infrared light of a wavelength absorbable by said compound; and (c) detecting fluorescence emitted by the compound wherein said fluorescence corresponds to the amyloid beta plaque contained in said sample;

wherein the compound exhibits increased fluorescence intensity upon binding to an amyloid beta plaque as compared to the fluorescence intensity exhibited by the compound when not bound to an amyloid beta plaque.

2. The method according to claim 1, wherein L is

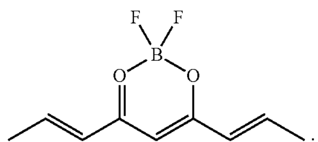

3. The method according to claim 2, wherein $Ar^1$ and $Ar^2$ are independently selected from

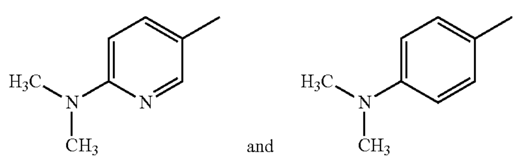

4. The method according to claim 3, wherein said compound has the structure:

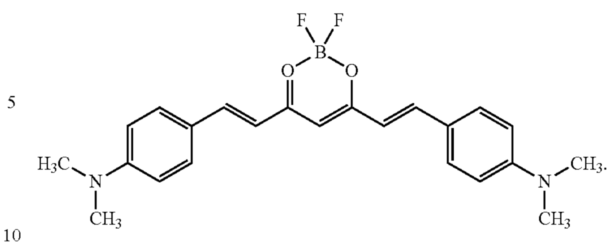

5. The method according to claim 1, wherein $Ar^1$ and $Ar^2$ are independently selected from

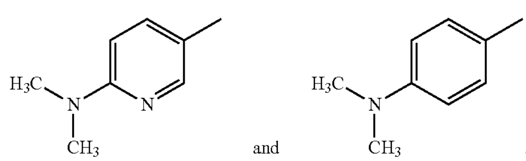

6. An in vivo optical imaging method for amyloid beta plaque detection, comprising:

(a) administering to a subject a compound, wherein said compound binds an amyloid beta plaque, wherein the compound has the formula $Ar^1$-L-$Ar^2$ and wherein: L is a divalent linking group comprising an alkenylene having 5 to 15 backbone carbon atoms, wherein at least two of the backbone carbon atoms form part of a difluoroboronate ring; and $Ar^1$ and $Ar^2$ are each independently alkyl amine-substituted aryl or heteroaryl groups;

(b) illuminating the subject with near infrared light of a wavelength absorbable by said compound; and (c) detecting fluorescence emitted by the compound wherein said fluorescence corresponds to the amyloid beta plaque present in the subject;

wherein the compound exhibits increased fluorescence intensity upon binding to an amyloid beta plaque as compared to the fluorescence intensity exhibited by the compound when not bound to an amyloid beta plaque.

7. The method according to claim 6, wherein L is

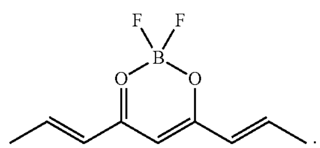

8. The method according to claim 7, wherein $Ar^1$ and $Ar^2$ are independently selected from

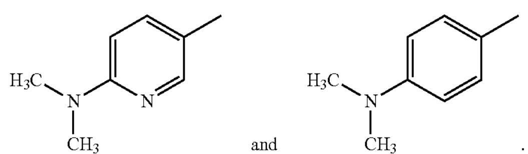

9. The method according to claim 8, wherein said compound has the structure:

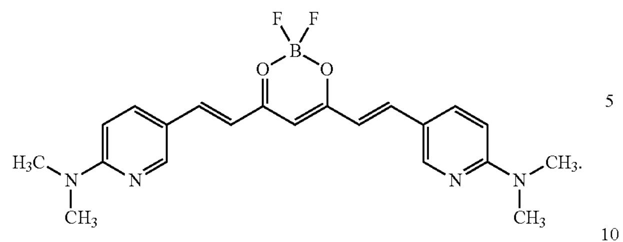

10. The method according to claim 6, wherein $Ar^1$ and $Ar^2$ are independently selected from

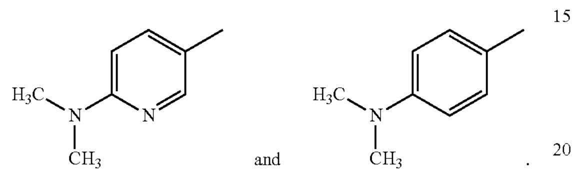

11. The method according to claim 6, wherein the fluorescence detected in step (c) is used in an additional step to construct an image of said amyloid beta plaque present in the subject.

12. The method according to claim 6, wherein step (c) is performed using a light detection or image recording component comprising a charge coupled device (CCD) system or photographic film.

* * * * *

UNITED STATES PATENT AND TRADEMARK OFFICE

CERTIFICATE OF CORRECTION

PATENT NO. : 10,149,644 B2
APPLICATION NO. : 14/515665
DATED : December 11, 2018
INVENTOR(S) : Chongzhao Ran and Anna Moore It is certified that error appears in the above-identified patent and that said Letters Patent is hereby corrected as shown below:

In the Claims

In Column 29, Lines 1-10, delete

"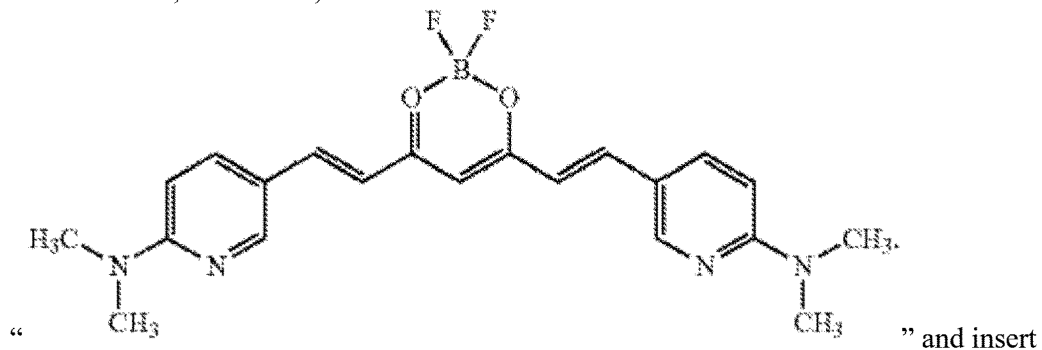

" and insert

-- 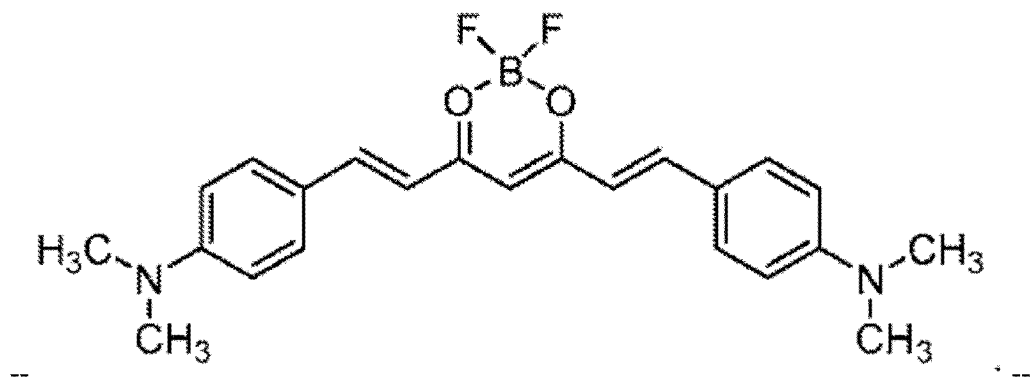

. --

Signed and Sealed this
Sixth Day of October, 2020

Andrei Iancu
*Director of the United States Patent and Trademark Office*